(12) United States Patent
Garbarino et al.

(10) Patent No.: US 6,448,391 B1
(45) Date of Patent: *Sep. 10, 2002

(54) UBIQUITIN-LYTIC PEPTIDE GENE PROMOTER

(75) Inventors: Joan Garbarino, Berkeley; William Belknap, Albany, both of CA (US)

(73) Assignees: The United States of America as represented by the Secretary of Agriculture, Washington, DC (US); Demegen, Inc., Pittsburgh, PA (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/482,611

(22) Filed: Jan. 14, 2000

Related U.S. Application Data

(63) Continuation of application No. 08/801,028, filed on Feb. 19, 1997, now Pat. No. 6,018,102, which is a continuation of application No. 08/279,472, filed on Jul. 22, 1994, now abandoned.

(51) Int. Cl.[7] .............................................. C07H 21/04
(52) U.S. Cl. ...................................................... 536/24.1
(58) Field of Search ............................ 535/23.1, 23.2, 535/24.1

(56) References Cited

U.S. PATENT DOCUMENTS

| | | | |
|---|---|---|---|
| 4,355,104 A | 10/1982 | Hultmark et al. | |
| 4,520,016 A | 5/1985 | Hultmark et al. | 514/12 |
| 4,810,777 A | 3/1989 | Zasloff et al. | 530/326 |
| 5,093,242 A | 3/1992 | Bachmair et al. | 435/69.7 |
| 5,132,213 A | 7/1992 | Bachmair et al. | 435/69.7 |
| 5,196,321 A | 3/1993 | Bachmair et al. | 435/69.7 |
| 5,294,605 A | 3/1994 | Houghten et al. | 514/13 |
| 5,357,044 A | 10/1994 | Lai et al. | 530/350 |

FOREIGN PATENT DOCUMENTS

| | | | |
|---|---|---|---|
| EP | 0 552 559 A2 | 7/1993 | C12N/15/62 |
| WO | WO 90/12866 | 11/1990 | C12N/1/06 |
| WO | WO 94/16076 | 7/1994 | C12N/15/29 |

OTHER PUBLICATIONS

GenBank Accession No. L22576 (Aug. 13, 1993).*
Hoffman et al. (1991) Plant Mol. Biol. 17: 1189–1201.
Ecker et al. (1989) Increasing Gene Expression in Yeast by Fusion to Ubiquitin. J. Biol. Chem 264(13): 7715–7719.
Copy of International Written Opinion dated Aug. 14, 1996 for related patent application No. PCT/US95/09339.
J. M. Jaynes, et al., In Vitro Cytocidal Effect of Lytic Peptides on Several Transformed Mammalian Cell Lines, *Peptide Research*, vol. 2, No. 2 (1989) pp. 157–160.
Jesse M. Jaynes, "Lytic Peptides Portend an Innovative Age in the Management and Treatment of Human Disease", *Drug News & Perspectives*, vol. 3, No. 2, Mar. 1990, pp. 69–78.
Karin S. Akerfeldt, et al., Synthetic Peptides as Models for Ion Channel Proteins, *Acc. Chem. Res.*, 1993, 26, pp. 191–197.
W. A. Reed, et al., "Enhanced In Vitro Growth of Murine Fibroblast Cells and Preimplantation Embryos Cultured in Medium Supplemented With an Amphipathic Peptide", *Molecular Reproduction and Development*, 31:106–113 (1992).
Michael J. Arrowood, et al., "Hemolytic Properties of Lytic Peptides Active Against the Sporozoites of Cryptosporidium parvum", *Workshop on Pneumocystis, Cryptosporidium and Microsporidia*, 161S–163–S.
Jesse M. Jaynes, et al., "In Vitro Cytocidal Effect of Novel Lytic Peptides on Plasmodium Falciparum and Trypanosoma Cruzi", *FASEB Journal*, vol. 2, No. 13, Oct. 1988, 2878–2883.
Jesse M. Jaynes, et al., "Expression of a Cecropin B Lytic Peptide Analog in Transgenic Tobacco Confers Enhanced Resistance to Bacterial Wilt Caused by Pseudomonas Solanacearum", *Plant Science*, 89 (1993) 43–53.
Luis Destefano–Beltran, et al., "Using Genes Encoding Novel Peptides and Proteins to Enhance Disease Resistance in Plants", *Biotechnology in Plant Disease Control*, pp. 175–189.
Joan E. Garbarino, et al., "Expression of Stress–Reponsive Ubiquitin Genes in Potato Tubers", *Plant Molecular Biology*, 20: 235–244, 1992.
Joan E. Garbarino, et al., "Isolation of a Ubiquitin–Ribosomal Protein Gene (ubi3) from Potato and Expression of its Promoter in Transgenic Plants", *Plant Molecular Biology*, 24: 119–127, 1994.

* cited by examiner

*Primary Examiner*—Ponnathapu Achutamurthy
*Assistant Examiner*—Kathleen Kerr
(74) *Attorney, Agent, or Firm*—Rothwell, Figg, Ernst & Manbeck; Margaret Connor; M. Howard Silverstein

(57) ABSTRACT

Stabilized ubiquitin-lytic peptide fusion polypeptides and a method of making the same by sub-cloning nucleic acid sequences coding for lytic peptides into a plasmid vector comprising a promoter and ubiquitin polypeptide coding sequence, wherein the ubiquitin polypeptide sequence is linked to the 5' end of the lytic peptide nucleic acid sequence and is translated as a fusion polypeptide.

2 Claims, 2 Drawing Sheets

SEQUENCE LISTING

<160> NUMBER OF SEQ ID NOS: 102

<210> SEQ ID NO 1
<211> LENGTH: 27
<212> TYPE: PRT
<213> ORGANISM: Artificial Sequence
<220> FEATURE:
<223> OTHER INFORMATION: Lytic Peptide

<400> SEQUENCE: 1

```
Phe Ala Val Ala Val Lys Ala Val Lys Lys Ala Val Lys Lys Val Lys
1               5                   10                  15

Lys Ala Val Lys Lys Ala Val Lys Lys Lys
            20                  25
```

<210> SEQ ID NO 2
<211> LENGTH: 32
<212> TYPE: PRT
<213> ORGANISM: Artificial Sequence
<220> FEATURE:
<223> OTHER INFORMATION: Lytic Peptide

<400> SEQUENCE: 2

```
Phe Ala Val Ala Val Lys Ala Val Ala Val Lys Ala Val Lys Lys Ala
1               5                   10                  15

Val Lys Lys Val Lys Lys Ala Val Lys Lys Ala Val Lys Lys Lys Lys
            20                  25                  30
```

<210> SEQ ID NO 3
<211> LENGTH: 37
<212> TYPE: PRT
<213> ORGANISM: Artificial Sequence
<220> FEATURE:
<223> OTHER INFORMATION: Lytic Peptide

<400> SEQUENCE: 3

```
Phe Ala Val Ala Val Lys Ala Val Ala Val Lys Ala Val Ala Val Lys
1               5                   10                  15

Ala Val Lys Lys Ala Val Lys Lys Val Lys Lys Ala Val Lys Lys Ala
```

```
              20                  25                  30
Val Lys Lys Lys Lys
        35

<210> SEQ ID NO 4
<211> LENGTH: 23
<212> TYPE: PRT
<213> ORGANISM: Artificial Sequence
<220> FEATURE:
<223> OTHER INFORMATION: Lytic Peptide

<400> SEQUENCE: 4

Phe Ala Val Ala Val Lys Ala Val Lys Lys Ala Val Lys Lys Val Lys
1               5                  10                  15

Lys Ala Val Lys Lys Ala Val
            20

<210> SEQ ID NO 5
<211> LENGTH: 28
<212> TYPE: PRT
<213> ORGANISM: Artificial Sequence
<220> FEATURE:
<223> OTHER INFORMATION: Lytic Peptide

<400> SEQUENCE: 5

Phe Ala Val Ala Val Lys Ala Val Ala Val Lys Ala Val Lys Lys Ala
1               5                  10                  15

Val Lys Lys Val Lys Lys Ala Val Lys Lys Ala Val
            20                  25

<210> SEQ ID NO 6
<211> LENGTH: 33
<212> TYPE: PRT
<213> ORGANISM: Artificial Sequence
<220> FEATURE:
<223> OTHER INFORMATION: Lytic Peptide

<400> SEQUENCE: 6

Phe Ala Val Ala Val Lys Ala Val Ala Val Lys Ala Val Ala Val Lys
1               5                  10                  15

Ala Val Lys Lys Ala Val Lys Lys Val Lys Lys Ala Val Lys Lys Ala
            20                  25                  30

Val

<210> SEQ ID NO 7
<211> LENGTH: 27
<212> TYPE: PRT
<213> ORGANISM: Artificial Sequence
<220> FEATURE:
<223> OTHER INFORMATION: Lytic Peptide

<400> SEQUENCE: 7

Phe Ala Val Gly Leu Arg Ala Ile Lys Arg Ala Leu Lys Lys Leu Arg
1               5                  10                  15

Arg Gly Val Arg Lys Val Ala Lys Arg Lys Arg
            20                  25

<210> SEQ ID NO 8
<211> LENGTH: 23
<212> TYPE: PRT
<213> ORGANISM: Artificial Sequence
<220> FEATURE:
<223> OTHER INFORMATION: Lytic Peptide
```

```
<400> SEQUENCE: 8

Phe Ala Val Gly Leu Arg Ala Ile Lys Arg Ala Leu Lys Lys Leu Arg
1               5                   10                  15

Arg Gly Val Arg Lys Val Ala
            20

<210> SEQ ID NO 9
<211> LENGTH: 27
<212> TYPE: PRT
<213> ORGANISM: Artificial Sequence
<220> FEATURE:
<223> OTHER INFORMATION: Lytic Peptide

<400> SEQUENCE: 9

Lys Arg Lys Arg Ala Val Lys Arg Val Gly Arg Leu Lys Lys Leu
1               5                   10                  15

Ala Arg Lys Ile Ala Arg Leu Gly Val Ala Phe
            20                  25

<210> SEQ ID NO 10
<211> LENGTH: 23
<212> TYPE: PRT
<213> ORGANISM: Artificial Sequence
<220> FEATURE:
<223> OTHER INFORMATION: Lytic Peptide

<400> SEQUENCE: 10

Ala Val Lys Arg Val Gly Arg Arg Leu Lys Leu Ala Arg Lys Ile
1               5                   10                  15

Ala Arg Leu Gly Val Ala Phe
            20

<210> SEQ ID NO 11
<211> LENGTH: 31
<212> TYPE: PRT
<213> ORGANISM: Artificial Sequence
<220> FEATURE:
<223> OTHER INFORMATION: Lytic Peptide

<400> SEQUENCE: 11

Phe Ala Val Gly Leu Arg Ala Ile Lys Arg Ala Leu Lys Lys Leu Arg
1               5                   10                  15

Arg Gly Val Arg Lys Val Ala Lys Arg Lys Lys Lys Asp Leu
            20                  25                  30

<210> SEQ ID NO 12
<211> LENGTH: 26
<212> TYPE: PRT
<213> ORGANISM: Artificial Sequence
<220> FEATURE:
<223> OTHER INFORMATION: Lytic Peptide

<400> SEQUENCE: 12

Phe Ala Val Gly Leu Arg Ala Ile Lys Arg Ala Leu Lys Lys Leu Arg
1               5                   10                  15

Arg Gly Val Arg Lys Val Ala Lys Asp Leu
            20                  25

<210> SEQ ID NO 13
<211> LENGTH: 30
<212> TYPE: PRT
<213> ORGANISM: Artificial Sequence
<220> FEATURE:
<223> OTHER INFORMATION: Lytic Peptide
```

```
<400> SEQUENCE: 13

Lys Arg Lys Arg Ala Val Lys Arg Val Gly Arg Arg Leu Lys Lys Leu
1               5                   10                  15

Ala Arg Lys Ile Ala Arg Leu Gly Val Ala Phe Lys Asp Leu
            20                  25                  30

<210> SEQ ID NO 14
<211> LENGTH: 26
<212> TYPE: PRT
<213> ORGANISM: Artificial Sequence
<220> FEATURE:
<223> OTHER INFORMATION: Lytic Peptide

<400> SEQUENCE: 14

Ala Val Lys Arg Val Gly Arg Arg Leu Lys Lys Leu Ala Arg Lys Ile
1               5                   10                  15

Ala Arg Leu Gly Val Ala Phe Lys Asp Leu
            20                  25

<210> SEQ ID NO 15
<211> LENGTH: 27
<212> TYPE: PRT
<213> ORGANISM: Artificial Sequence
<220> FEATURE:
<223> OTHER INFORMATION: Lytic Peptide

<400> SEQUENCE: 15

Lys Lys Lys Lys Phe Val Lys Val Ala Lys Val Lys Val
1               5                   10                  15

Ala Lys Lys Val Ala Lys Val Ala Val Ala Val
            20                  25

<210> SEQ ID NO 16
<211> LENGTH: 32
<212> TYPE: PRT
<213> ORGANISM: Artificial Sequence
<220> FEATURE:
<223> OTHER INFORMATION: Lytic Peptide

<400> SEQUENCE: 16

Lys Lys Lys Lys Phe Val Lys Val Ala Lys Val Lys Val
1               5                   10                  15

Ala Lys Lys Val Ala Lys Val Ala Val Ala Lys Val Ala Val Ala Val
            20                  25                  30

<210> SEQ ID NO 17
<211> LENGTH: 37
<212> TYPE: PRT
<213> ORGANISM: Artificial Sequence
<220> FEATURE:
<223> OTHER INFORMATION: Lytic Peptide

<400> SEQUENCE: 17

Lys Lys Lys Lys Phe Val Lys Val Ala Lys Val Lys Val
1               5                   10                  15

Ala Lys Lys Val Ala Lys Val Ala Val Ala Lys Val Ala Val Ala Lys
            20                  25                  30

Val Ala Val Ala Val
        35

<210> SEQ ID NO 18
<211> LENGTH: 23
```

```
<212> TYPE: PRT
<213> ORGANISM: Artificial Sequence
<220> FEATURE:
<223> OTHER INFORMATION: Lytic Peptide

<400> SEQUENCE: 18

Phe Val Lys Lys Val Ala Lys Lys Val Lys Lys Val Ala Lys Lys Val
1               5                   10                  15

Ala Lys Val Ala Val Ala Val
            20

<210> SEQ ID NO 19
<211> LENGTH: 28
<212> TYPE: PRT
<213> ORGANISM: Artificial Sequence
<220> FEATURE:
<223> OTHER INFORMATION: Lytic Peptide

<400> SEQUENCE: 19

Phe Val Lys Lys Val Ala Lys Lys Val Lys Lys Val Ala Lys Lys Val
1               5                   10                  15

Ala Lys Val Ala Val Ala Lys Val Ala Val Ala Val
            20                  25

<210> SEQ ID NO 20
<211> LENGTH: 33
<212> TYPE: PRT
<213> ORGANISM: Artificial Sequence
<220> FEATURE:
<223> OTHER INFORMATION: Lytic Peptide

<400> SEQUENCE: 20

Phe Val Lys Lys Val Ala Lys Lys Val Lys Lys Val Ala Lys Lys Val
1               5                   10                  15

Ala Lys Val Ala Val Ala Lys Val Ala Val Ala Lys Val Ala Val Ala
            20                  25                  30

Val

<210> SEQ ID NO 21
<211> LENGTH: 27
<212> TYPE: PRT
<213> ORGANISM: Artificial Sequence
<220> FEATURE:
<223> OTHER INFORMATION: Lytic Peptide

<400> SEQUENCE: 21

Lys Lys Lys Lys Phe Val Lys Val Ala Lys Val Ala Lys Lys Val
1               5                   10                  15

Ala Lys Val Ala Lys Lys Val Ala Lys Lys Val
            20                  25

<210> SEQ ID NO 22
<211> LENGTH: 32
<212> TYPE: PRT
<213> ORGANISM: Artificial Sequence
<220> FEATURE:
<223> OTHER INFORMATION: Lytic Peptide

<400> SEQUENCE: 22

Lys Lys Lys Lys Phe Val Lys Val Ala Lys Val Ala Lys Lys Val
1               5                   10                  15

Ala Lys Val Ala Lys Lys Val Ala Lys Lys Val Ala Lys Lys Val Ala
            20                  25                  30
```

<210> SEQ ID NO 23
<211> LENGTH: 37
<212> TYPE: PRT
<213> ORGANISM: Artificial Sequence
<220> FEATURE:
<223> OTHER INFORMATION: Lytic Peptide

<400> SEQUENCE: 23

```
Lys Lys Lys Lys Phe Val Lys Val Ala Lys Val Ala Lys Val
1               5                  10                  15

Ala Lys Val Ala Lys Lys Val Ala Lys Lys Val Ala Lys Val Ala
            20                  25                  30

Lys Val Ala Lys Lys
        35
```

<210> SEQ ID NO 24
<211> LENGTH: 23
<212> TYPE: PRT
<213> ORGANISM: Artificial Sequence
<220> FEATURE:
<223> OTHER INFORMATION: Lytic Peptide

<400> SEQUENCE: 24

```
Phe Val Lys Lys Val Ala Lys Val Ala Lys Lys Val Ala Lys Val Ala
1               5                  10                  15

Lys Lys Val Ala Lys Lys Val
            20
```

<210> SEQ ID NO 25
<211> LENGTH: 28
<212> TYPE: PRT
<213> ORGANISM: Artificial Sequence
<220> FEATURE:
<223> OTHER INFORMATION: Lytic Peptide

<400> SEQUENCE: 25

```
Phe Val Lys Lys Val Ala Lys Val Ala Lys Lys Val Ala Lys Val Ala
1               5                  10                  15

Lys Lys Val Ala Lys Lys Val Ala Lys Lys Val Ala
            20                  25
```

<210> SEQ ID NO 26
<211> LENGTH: 33
<212> TYPE: PRT
<213> ORGANISM: Artificial Sequence
<220> FEATURE:
<223> OTHER INFORMATION: Lytic Peptide

<400> SEQUENCE: 26

```
Phe Val Lys Lys Val Ala Lys Val Ala Lys Lys Val Ala Lys Val Ala
1               5                  10                  15

Lys Lys Val Ala Lys Lys Val Ala Lys Lys Val Ala Lys Val Ala Lys
            20                  25                  30

Lys
```

<210> SEQ ID NO 27
<211> LENGTH: 27
<212> TYPE: PRT
<213> ORGANISM: Artificial Sequence
<220> FEATURE:
<223> OTHER INFORMATION: Lytic Peptide

<400> SEQUENCE: 27

Phe Val Lys Lys Val Ala Lys Val Ala Lys Lys Val Ala Lys Val Ala
1               5                   10                  15

Lys Lys Val Ala Lys Lys Val Lys Lys Lys
            20                  25

<210> SEQ ID NO 28
<211> LENGTH: 32
<212> TYPE: PRT
<213> ORGANISM: Artificial Sequence
<220> FEATURE:
<223> OTHER INFORMATION: Lytic Peptide

<400> SEQUENCE: 28

Phe Val Lys Lys Val Ala Lys Val Ala Lys Lys Val Ala Lys Val Ala
1               5                   10                  15

Lys Lys Val Ala Lys Lys Val Ala Lys Lys Val Ala Lys Lys Lys Lys
            20                  25                  30

<210> SEQ ID NO 29
<211> LENGTH: 37
<212> TYPE: PRT
<213> ORGANISM: Artificial Sequence
<220> FEATURE:
<223> OTHER INFORMATION: Lytic Peptide

<400> SEQUENCE: 29

Phe Val Lys Lys Val Ala Lys Val Ala Lys Lys Val Ala Lys Val Ala
1               5                   10                  15

Lys Lys Val Ala Lys Lys Val Ala Lys Lys Val Ala Lys Val Ala Lys
            20                  25                  30

Lys Lys Lys Lys Lys
        35

<210> SEQ ID NO 30
<211> LENGTH: 16
<212> TYPE: PRT
<213> ORGANISM: Artificial Sequence
<220> FEATURE:
<223> OTHER INFORMATION: Lytic Peptide

<400> SEQUENCE: 30

Phe Lys Val Lys Ala Lys Val Lys Ala Lys Val Lys Lys Lys Lys Lys
1               5                   10                  15

<210> SEQ ID NO 31
<211> LENGTH: 21
<212> TYPE: PRT
<213> ORGANISM: Artificial Sequence
<220> FEATURE:
<223> OTHER INFORMATION: Lytic Peptide

<400> SEQUENCE: 31

Phe Lys Val Lys Ala Lys Val Lys Ala Lys Val Lys Ala Lys Val Lys
1               5                   10                  15

Ala Lys Lys Lys Lys
        20

<210> SEQ ID NO 32
<211> LENGTH: 27
<212> TYPE: PRT
<213> ORGANISM: Artificial Sequence
<220> FEATURE:
<223> OTHER INFORMATION: Lytic Peptide

<400> SEQUENCE: 32

```
Phe Lys Val Lys Ala Lys Val Lys Ala Lys Val Lys Ala Lys Val Lys
1               5                   10                  15

Ala Lys Val Lys Ala Lys Val Lys Lys Lys
            20                  25
```

<210> SEQ ID NO 33
<211> LENGTH: 12
<212> TYPE: PRT
<213> ORGANISM: Artificial Sequence
<220> FEATURE:
<223> OTHER INFORMATION: Lytic Peptide

<400> SEQUENCE: 33

```
Phe Lys Val Lys Ala Lys Val Lys Ala Lys Val Lys
1               5                   10
```

<210> SEQ ID NO 34
<211> LENGTH: 17
<212> TYPE: PRT
<213> ORGANISM: Artificial Sequence
<220> FEATURE:
<223> OTHER INFORMATION: Lytic Peptide

<400> SEQUENCE: 34

```
Phe Lys Val Lys Ala Lys Val Lys Ala Lys Val Lys Ala Lys Val Lys
1               5                   10                  15

Ala
```

<210> SEQ ID NO 35
<211> LENGTH: 23
<212> TYPE: PRT
<213> ORGANISM: Artificial Sequence
<220> FEATURE:
<223> OTHER INFORMATION: Lytic Peptide

<400> SEQUENCE: 35

```
Phe Lys Val Lys Ala Lys Val Lys Ala Lys Val Lys Ala Lys Val Lys
1               5                   10                  15

Ala Lys Val Lys Ala Lys Val
            20
```

<210> SEQ ID NO 36
<211> LENGTH: 16
<212> TYPE: PRT
<213> ORGANISM: Artificial Sequence
<220> FEATURE:
<223> OTHER INFORMATION: Lytic Peptide

<400> SEQUENCE: 36

```
Lys Lys Lys Lys Phe Lys Val Lys Ala Lys Val Lys Ala Lys Val Lys
1               5                   10                  15
```

<210> SEQ ID NO 37
<211> LENGTH: 21
<212> TYPE: PRT
<213> ORGANISM: Artificial Sequence
<220> FEATURE:
<223> OTHER INFORMATION: Lytic Peptide

<400> SEQUENCE: 37

```
Lys Lys Lys Lys Phe Lys Val Lys Ala Lys Val Lys Ala Lys Val Lys
1               5                   10                  15

Ala Lys Val Lys Ala
            20
```

<210> SEQ ID NO 38
<211> LENGTH: 27
<212> TYPE: PRT
<213> ORGANISM: Artificial Sequence
<220> FEATURE:
<223> OTHER INFORMATION: Lytic Peptide

<400> SEQUENCE: 38

Lys Lys Lys Lys Phe Lys Val Lys Ala Lys Val Lys Ala Lys Val Lys
1               5                   10                  15

Ala Lys Val Lys Ala Lys Val Lys Ala Lys Val
            20                  25

<210> SEQ ID NO 39
<211> LENGTH: 25
<212> TYPE: PRT
<213> ORGANISM: Artificial Sequence
<220> FEATURE:
<223> OTHER INFORMATION: Lytic Peptide

<400> SEQUENCE: 39

Phe Lys Lys Val Lys Lys Val Ala Lys Val Cys Lys Cys Val Lys
1               5                   10                  15

Lys Ala Val Lys Lys Val Lys Lys Phe
            20                  25

<210> SEQ ID NO 40
<211> LENGTH: 27
<212> TYPE: PRT
<213> ORGANISM: Artificial Sequence
<220> FEATURE:
<223> OTHER INFORMATION: Lytic Peptide

<400> SEQUENCE: 40

Phe Ala Val Ala Val Lys Ala Val Lys Lys Ala Val Lys Lys Val Lys
1               5                   10                  15

Lys Ala Val Lys Lys Ala Val Cys Cys Cys Cys
            20                  25

<210> SEQ ID NO 41
<211> LENGTH: 27
<212> TYPE: PRT
<213> ORGANISM: Artificial Sequence
<220> FEATURE:
<223> OTHER INFORMATION: Lytic Peptide

<400> SEQUENCE: 41

Cys Cys Cys Cys Phe Val Lys Lys Val Ala Lys Val Lys Lys Val
1               5                   10                  15

Ala Lys Lys Val Ala Lys Val Ala Val Ala Val
            20                  25

<210> SEQ ID NO 42
<211> LENGTH: 27
<212> TYPE: PRT
<213> ORGANISM: Artificial Sequence
<220> FEATURE:
<223> OTHER INFORMATION: Lytic Peptide

<400> SEQUENCE: 42

Phe Ala Val Ala Val Lys Ala Val Lys Lys Ala Val Lys Lys Val Lys
1               5                   10                  15

Lys Ala Val Lys Lys Ala Val Ser Ser Ser Ser

```
                    20                  25

<210> SEQ ID NO 43
<211> LENGTH: 27
<212> TYPE: PRT
<213> ORGANISM: Artificial Sequence
<220> FEATURE:
<223> OTHER INFORMATION: Lytic Peptide

<400> SEQUENCE: 43

Ser Ser Ser Ser Phe Val Lys Lys Val Ala Lys Lys Val Lys Lys Val
1               5                   10                  15

Ala Lys Lys Val Ala Lys Val Ala Val Ala Val
            20                  25

<210> SEQ ID NO 44
<211> LENGTH: 23
<212> TYPE: PRT
<213> ORGANISM: Artificial Sequence
<220> FEATURE:
<223> OTHER INFORMATION: Lytic Peptide

<400> SEQUENCE: 44

Phe Ala Leu Ala Leu Lys Ala Leu Lys Lys Ala Leu Lys Lys Leu Lys
1               5                   10                  15

Lys Ala Leu Lys Lys Ala Leu
            20

<210> SEQ ID NO 45
<211> LENGTH: 23
<212> TYPE: PRT
<213> ORGANISM: Artificial Sequence
<220> FEATURE:
<223> OTHER INFORMATION: Lytic Peptide

<400> SEQUENCE: 45

Leu Ala Lys Lys Leu Ala Lys Lys Leu Lys Lys Leu Ala Lys Lys Leu
1               5                   10                  15

Ala Lys Leu Ala Leu Ala Phe
            20

<210> SEQ ID NO 46
<211> LENGTH: 23
<212> TYPE: PRT
<213> ORGANISM: Artificial Sequence
<220> FEATURE:
<223> OTHER INFORMATION: Lytic Peptide

<400> SEQUENCE: 46

Phe Ala Phe Ala Phe Lys Ala Phe Lys Lys Ala Phe Lys Lys Phe Lys
1               5                   10                  15

Lys Ala Phe Lys Lys Ala Phe
            20

<210> SEQ ID NO 47
<211> LENGTH: 23
<212> TYPE: PRT
<213> ORGANISM: Artificial Sequence
<220> FEATURE:
<223> OTHER INFORMATION: Lytic Peptide

<400> SEQUENCE: 47

Phe Ala Ile Ala Ile Lys Ala Ile Lys Lys Ala Ile Lys Lys Ile Lys
1               5                   10                  15
```

Lys Ala Ile Lys Lys Ala Ile
            20

<210> SEQ ID NO 48
<211> LENGTH: 23
<212> TYPE: PRT
<213> ORGANISM: Artificial Sequence
<220> FEATURE:
<223> OTHER INFORMATION: Lytic Peptide

<400> SEQUENCE: 48

Phe Ala Lys Lys Phe Ala Lys Lys Phe Lys Phe Ala Lys Lys Phe
1               5                   10                  15

Ala Lys Phe Ala Phe Ala Phe
            20

<210> SEQ ID NO 49
<211> LENGTH: 17
<212> TYPE: PRT
<213> ORGANISM: Artificial Sequence
<220> FEATURE:
<223> OTHER INFORMATION: Lytic Peptide

<400> SEQUENCE: 49

Phe Lys Arg Leu Ala Lys Ile Lys Val Leu Arg Leu Ala Lys Ile Lys
1               5                   10                  15

Arg

<210> SEQ ID NO 50
<211> LENGTH: 37
<212> TYPE: PRT
<213> ORGANISM: Artificial Sequence
<220> FEATURE:
<223> OTHER INFORMATION: Lytic Peptide

<400> SEQUENCE: 50

Lys Leu Lys Leu Ala Val Lys Leu Val Gly Leu Leu Arg Lys Lys Arg
1               5                   10                  15

Ala Leu Lys Ile Ala Leu Arg Gly Val Ala Lys Arg Ala Gly Arg Leu
            20                  25                  30

Ala Val Arg Lys Phe
            35

<210> SEQ ID NO 51
<211> LENGTH: 26
<212> TYPE: PRT
<213> ORGANISM: Artificial Sequence
<220> FEATURE:
<223> OTHER INFORMATION: Lytic Peptide

<400> SEQUENCE: 51

Phe Ala Arg Ala Arg Lys Ala Arg Lys Lys Ala Arg Lys Arg Lys
1               5                   10                  15

Lys Ala Arg Lys Lys Ala Arg Lys Asp Arg
            20                  25

<210> SEQ ID NO 52
<211> LENGTH: 23
<212> TYPE: PRT
<213> ORGANISM: Artificial Sequence
<220> FEATURE:
<223> OTHER INFORMATION: Lytic Peptide

<400> SEQUENCE: 52

Phe Ala Val Ala Val Cys Ala Val Cys Cys Ala Val Cys Cys Val Cys
1               5                   10                  15

Cys Ala Val Cys Cys Ala Val
            20

<210> SEQ ID NO 53
<211> LENGTH: 23
<212> TYPE: PRT
<213> ORGANISM: Artificial Sequence
<220> FEATURE:
<223> OTHER INFORMATION: Lytic Peptide

<400> SEQUENCE: 53

Phe Ala Val Ala Val Ser Ala Val Ser Ser Ala Val Ser Ser Val Ser
1               5                   10                  15

Ser Ala Val Ser Ser Ala Val
            20

<210> SEQ ID NO 54
<211> LENGTH: 27
<212> TYPE: PRT
<213> ORGANISM: Artificial Sequence
<220> FEATURE:
<223> OTHER INFORMATION: Lytic Peptide

<400> SEQUENCE: 54

Phe Ala Val Ala Val Ser Ala Val Ser Ser Ala Val Ser Ser Val Ser
1               5                   10                  15

Ser Ala Val Ser Ser Ala Val Ser Ser Ser
            20                  25

<210> SEQ ID NO 55
<211> LENGTH: 27
<212> TYPE: PRT
<213> ORGANISM: Artificial Sequence
<220> FEATURE:
<223> OTHER INFORMATION: Lytic Peptide

<400> SEQUENCE: 55

Phe Ala Lys Lys Phe Ala Lys Lys Phe Lys Lys Phe Ala Lys Lys Phe
1               5                   10                  15

Ala Lys Phe Ala Phe Ala Phe Lys Lys Lys
            20                  25

<210> SEQ ID NO 56
<211> LENGTH: 27
<212> TYPE: PRT
<213> ORGANISM: Artificial Sequence
<220> FEATURE:
<223> OTHER INFORMATION: Lytic Peptide

<400> SEQUENCE: 56

Lys Lys Lys Lys Phe Ala Lys Lys Phe Ala Lys Lys Phe Lys Lys Phe
1               5                   10                  15

Ala Lys Lys Phe Ala Lys Phe Ala Phe Ala Phe
            20                  25

<210> SEQ ID NO 57
<211> LENGTH: 23
<212> TYPE: PRT
<213> ORGANISM: Artificial Sequence
<220> FEATURE:
<223> OTHER INFORMATION: Lytic Peptide

<400> SEQUENCE: 57

Phe Ala Arg Lys Phe Leu Lys Arg Phe Lys Lys Phe Val Arg Lys Phe
1               5                   10                  15

Ile Arg Phe Ala Phe Leu Phe
            20

<210> SEQ ID NO 58
<211> LENGTH: 27
<212> TYPE: PRT
<213> ORGANISM: Artificial Sequence
<220> FEATURE:
<223> OTHER INFORMATION: Lytic Peptide

<400> SEQUENCE: 58

Phe Ala Arg Lys Phe Leu Lys Arg Phe Lys Lys Phe Val Arg Lys Phe
1               5                   10                  15

Ile Arg Phe Ala Phe Leu Phe Lys Arg Lys Arg
            20                  25

<210> SEQ ID NO 59
<211> LENGTH: 27
<212> TYPE: PRT
<213> ORGANISM: Artificial Sequence
<220> FEATURE:
<223> OTHER INFORMATION: Lytic Peptide

<400> SEQUENCE: 59

Lys Arg Lys Arg Phe Ala Arg Lys Phe Leu Arg Phe Lys Lys Phe
1               5                   10                  15

Val Arg Lys Phe Ile Arg Phe Ala Phe Leu Phe
            20                  25

<210> SEQ ID NO 60
<211> LENGTH: 23
<212> TYPE: PRT
<213> ORGANISM: Artificial Sequence
<220> FEATURE:
<223> OTHER INFORMATION: Lytic Peptide

<400> SEQUENCE: 60

Ile Ala Lys Lys Ile Ala Lys Lys Ile Lys Lys Ile Ala Lys Lys Ile
1               5                   10                  15

Ala Lys Ile Ala Ile Ala Ile
            20

<210> SEQ ID NO 61
<211> LENGTH: 27
<212> TYPE: PRT
<213> ORGANISM: Artificial Sequence
<220> FEATURE:
<223> OTHER INFORMATION: Lytic Peptide

<400> SEQUENCE: 61

Ile Ala Lys Lys Ile Ala Lys Lys Ile Lys Lys Ile Ala Lys Lys Ile
1               5                   10                  15

Ala Lys Ile Ala Ile Ala Ile Lys Lys Lys Lys
            20                  25

<210> SEQ ID NO 62
<211> LENGTH: 27
<212> TYPE: PRT
<213> ORGANISM: Artificial Sequence
<220> FEATURE:
<223> OTHER INFORMATION: Lytic Peptide

<400> SEQUENCE: 62

Lys Lys Lys Lys Ile Ala Lys Ile Ala Lys Ile Lys Ile
1               5                   10                  15

Ala Lys Lys Ile Ala Lys Ile Ala Ile
            20                  25

<210> SEQ ID NO 63
<211> LENGTH: 23
<212> TYPE: PRT
<213> ORGANISM: Artificial Sequence
<220> FEATURE:
<223> OTHER INFORMATION: Lytic Peptide

<400> SEQUENCE: 63

Ile Ala Arg Lys Ile Leu Lys Arg Ile Lys Ile Val Arg Lys Phe
1               5                   10                  15

Ile Arg Ile Ala Ile Leu Ile
            20

<210> SEQ ID NO 64
<211> LENGTH: 27
<212> TYPE: PRT
<213> ORGANISM: Artificial Sequence
<220> FEATURE:
<223> OTHER INFORMATION: Lytic Peptide

<400> SEQUENCE: 64

Ile Ala Arg Lys Ile Leu Lys Arg Ile Lys Ile Val Arg Lys Phe
1               5                   10                  15

Ile Arg Ile Ala Ile Leu Ile Lys Arg Lys Arg
            20                  25

<210> SEQ ID NO 65
<211> LENGTH: 27
<212> TYPE: PRT
<213> ORGANISM: Artificial Sequence
<220> FEATURE:
<223> OTHER INFORMATION: Lytic Peptide

<400> SEQUENCE: 65

Lys Arg Lys Arg Ile Ala Arg Lys Ile Leu Lys Arg Ile Lys Ile
1               5                   10                  15

Val Arg Lys Phe Ile Arg Ile Ala Ile Leu Ile
            20                  25

<210> SEQ ID NO 66
<211> LENGTH: 17
<212> TYPE: PRT
<213> ORGANISM: Artificial Sequence
<220> FEATURE:
<223> OTHER INFORMATION: Lytic Peptide

<400> SEQUENCE: 66

Phe Lys Leu Arg Ala Lys Ile Lys Val Arg Leu Arg Ala Lys Ile Lys
1               5                   10                  15

Leu

<210> SEQ ID NO 67
<211> LENGTH: 21
<212> TYPE: PRT
<213> ORGANISM: Artificial Sequence
<220> FEATURE:
<223> OTHER INFORMATION: Lytic Peptide -continued

```
<400> SEQUENCE: 67

Lys Arg Lys Arg Phe Lys Leu Arg Ala Lys Ile Lys Val Arg Leu Arg
1               5                   10                  15

Ala Lys Ile Lys Leu
            20

<210> SEQ ID NO 68
<211> LENGTH: 21
<212> TYPE: PRT
<213> ORGANISM: Artificial Sequence
<220> FEATURE:
<223> OTHER INFORMATION: Lytic Peptide

<400> SEQUENCE: 68

Phe Lys Leu Arg Ala Lys Ile Lys Val Arg Leu Arg Ala Lys Ile Lys
1               5                   10                  15

Leu Lys Arg Lys Arg
            20

<210> SEQ ID NO 69
<211> LENGTH: 23
<212> TYPE: PRT
<213> ORGANISM: Artificial Sequence
<220> FEATURE:
<223> OTHER INFORMATION: Lytic Peptide

<400> SEQUENCE: 69

Phe Lys Leu Arg Ala Lys Ile Lys Val Arg Leu Arg Ala Lys Ile Lys
1               5                   10                  15

Leu Arg Val Lys Leu Lys Ile
            20

<210> SEQ ID NO 70
<211> LENGTH: 27
<212> TYPE: PRT
<213> ORGANISM: Artificial Sequence
<220> FEATURE:
<223> OTHER INFORMATION: Lytic Peptide

<400> SEQUENCE: 70

Phe Lys Leu Arg Ala Lys Ile Lys Val Arg Leu Arg Ala Lys Ile Lys
1               5                   10                  15

Leu Arg Val Lys Leu Lys Ile Lys Arg Lys Arg
            20                  25

<210> SEQ ID NO 71
<211> LENGTH: 27
<212> TYPE: PRT
<213> ORGANISM: Artificial Sequence
<220> FEATURE:
<223> OTHER INFORMATION: Lytic Peptide

<400> SEQUENCE: 71

Lys Arg Lys Arg Phe Lys Leu Arg Ala Lys Ile Lys Val Arg Leu Arg
1               5                   10                  15

Ala Lys Ile Lys Leu Arg Val Lys Leu Lys Ile
            20                  25

<210> SEQ ID NO 72
<211> LENGTH: 29
<212> TYPE: PRT
<213> ORGANISM: Artificial Sequence
<220> FEATURE:
<223> OTHER INFORMATION: Lytic Peptide
```

```
<400> SEQUENCE: 72

Phe Lys Leu Arg Ala Lys Ile Lys Val Arg Leu Arg Ala Lys Ile Lys
1               5                   10                  15
Leu Arg Val Lys Leu Lys Ile Arg Ala Arg Ile Lys Leu
            20                  25

<210> SEQ ID NO 73
<211> LENGTH: 33
<212> TYPE: PRT
<213> ORGANISM: Artificial Sequence
<220> FEATURE:
<223> OTHER INFORMATION: Lytic Peptide

<400> SEQUENCE: 73

Phe Lys Leu Arg Ala Lys Ile Lys Val Arg Leu Arg Ala Lys Ile Lys
1               5                   10                  15
Leu Arg Val Lys Leu Lys Ile Arg Ala Arg Ile Lys Leu Lys Arg Lys
            20                  25                  30
    Arg

<210> SEQ ID NO 74
<211> LENGTH: 33
<212> TYPE: PRT
<213> ORGANISM: Artificial Sequence
<220> FEATURE:
<223> OTHER INFORMATION: Lytic Peptide

<400> SEQUENCE: 74

Lys Arg Lys Arg Phe Lys Leu Arg Ala Lys Ile Lys Val Arg Leu Arg
1               5                   10                  15
Ala Lys Ile Lys Leu Arg Val Lys Leu Lys Ile Arg Ala Arg Ile Lys
            20                  25                  30
Leu

<210> SEQ ID NO 75
<211> LENGTH: 23
<212> TYPE: PRT
<213> ORGANISM: Artificial Sequence
<220> FEATURE:
<223> OTHER INFORMATION: Lytic Peptide

<400> SEQUENCE: 75

Phe Lys Leu Arg Ala Lys Ile Lys Val Arg Leu Arg Ala Lys Ile Lys
1               5                   10                  15
Leu Val Phe Ala Ile Leu Leu
            20

<210> SEQ ID NO 76
<211> LENGTH: 27
<212> TYPE: PRT
<213> ORGANISM: Artificial Sequence
<220> FEATURE:
<223> OTHER INFORMATION: Lytic Peptide

<400> SEQUENCE: 76

Phe Lys Leu Arg Ala Lys Ile Lys Val Arg Leu Arg Ala Lys Ile Lys
1               5                   10                  15
Leu Val Phe Ala Ile Leu Leu Lys Arg Lys Arg
            20                  25

<210> SEQ ID NO 77
<211> LENGTH: 27
```

<212> TYPE: PRT
<213> ORGANISM: Artificial Sequence
<220> FEATURE:
<223> OTHER INFORMATION: Lytic Peptide

<400> SEQUENCE: 77

Lys Arg Lys Arg Phe Lys Leu Arg Ala Lys Ile Lys Val Arg Leu Arg
1               5                   10                  15

Ala Lys Ile Lys Leu Val Phe Ala Ile Leu Leu
            20                  25

<210> SEQ ID NO 78
<211> LENGTH: 23
<212> TYPE: PRT
<213> ORGANISM: Artificial Sequence
<220> FEATURE:
<223> OTHER INFORMATION: Lytic Peptide

<400> SEQUENCE: 78

Val Phe Ala Ile Leu Leu Phe Lys Leu Arg Ala Lys Ile Lys Val Arg
1               5                   10                  15

Leu Arg Ala Lys Ile Lys Leu
            20

<210> SEQ ID NO 79
<211> LENGTH: 27
<212> TYPE: PRT
<213> ORGANISM: Artificial Sequence
<220> FEATURE:
<223> OTHER INFORMATION: Lytic Peptide

<400> SEQUENCE: 79

Val Phe Ala Ile Leu Leu Phe Lys Leu Arg Ala Lys Ile Lys Val Arg
1               5                   10                  15

Leu Arg Ala Lys Ile Lys Leu Lys Arg Lys Arg
            20                  25

<210> SEQ ID NO 80
<211> LENGTH: 27
<212> TYPE: PRT
<213> ORGANISM: Artificial Sequence
<220> FEATURE:
<223> OTHER INFORMATION: Lytic Peptide

<400> SEQUENCE: 80

Lys Arg Lys Arg Val Phe Ala Ile Leu Leu Phe Lys Leu Arg Ala Lys
1               5                   10                  15

Ile Lys Val Arg Leu Arg Ala Lys Ile Lys Leu
            20                  25

<210> SEQ ID NO 81
<211> LENGTH: 29
<212> TYPE: PRT
<213> ORGANISM: Artificial Sequence
<220> FEATURE:
<223> OTHER INFORMATION: Lytic Peptide

<400> SEQUENCE: 81

Val Gly Glu Cys Val Arg Gly Arg Cys Pro Ser Gly Met Cys Cys Ser
1               5                   10                  15

Gln Phe Gly Tyr Cys Gly Lys Gly Pro Lys Tyr Cys Gly
            20                  25

<210> SEQ ID NO 82

<210> SEQ ID NO 82
<211> LENGTH: 30
<212> TYPE: PRT
<213> ORGANISM: Artificial Sequence
<220> FEATURE:
<223> OTHER INFORMATION: Lytic Peptide

<400> SEQUENCE: 82

```
Val Gly Glu Cys Val Arg Gly Arg Cys Pro Ser Gly Met Cys Cys Ser
 1               5                  10                  15
Gln Phe Gly Tyr Cys Gly Lys Gly Pro Lys Tyr Cys Gly Arg
            20                  25                  30
```

<210> SEQ ID NO 83
<211> LENGTH: 30
<212> TYPE: PRT
<213> ORGANISM: Artificial Sequence
<220> FEATURE:
<223> OTHER INFORMATION: Lytic Peptide

<400> SEQUENCE: 83

```
Leu Gly Asp Cys Leu Lys Gly Lys Cys Pro Ser Gly Met Cys Cys Ser
 1               5                  10                  15
Asn Tyr Gly Phe Cys Gly Arg Gly Pro Arg Phe Cys Gly Lys
            20                  25                  30
```

<210> SEQ ID NO 84
<211> LENGTH: 37
<212> TYPE: PRT
<213> ORGANISM: Artificial Sequence
<220> FEATURE:
<223> OTHER INFORMATION: Lytic Peptide

<400> SEQUENCE: 84

```
Gln Cys Ile Gly Asn Gly Gly Arg Cys Asn Glu Asn Val Gly Pro Pro
 1               5                  10                  15
Tyr Cys Cys Ser Gly Phe Cys Leu Arg Gln Pro Gly Gln Gly Tyr Gly
            20                  25                  30
Tyr Cys Lys Asn Arg
        35
```

<210> SEQ ID NO 85
<211> LENGTH: 36
<212> TYPE: PRT
<213> ORGANISM: Artificial Sequence
<220> FEATURE:
<223> OTHER INFORMATION: Lytic Peptide

<400> SEQUENCE: 85

```
Cys Ile Gly Asn Gly Gly Arg Cys Asn Glu Asn Val Gly Pro Pro Tyr
 1               5                  10                  15
Cys Cys Ser Gly Phe Cys Leu Arg Gln Pro Asn Gln Gly Tyr Gly Val
            20                  25                  30
Cys Arg Asn Arg
        35
```

<210> SEQ ID NO 86
<211> LENGTH: 36
<212> TYPE: PRT
<213> ORGANISM: Artificial Sequence
<220> FEATURE:
<223> OTHER INFORMATION: Lytic Peptide

<400> SEQUENCE: 86

```
Cys Ile Gly Gln Gly Gly Lys Cys Gln Asp Gln Leu Gly Pro Pro Phe
```

```
                1               5              10              15
Cys Cys Ser Gly Tyr Cys Val Lys Asn Pro Gln Asn Gly Phe Gly Leu
                        20                  25                  30

Cys Lys Gln Lys
            35
```

<210> SEQ ID NO 87
<211> LENGTH: 44
<212> TYPE: PRT
<213> ORGANISM: Artificial Sequence
<220> FEATURE:
<223> OTHER INFORMATION: Lytic Peptide

<400> SEQUENCE: 87

```
Gln Lys Leu Cys Glu Arg Pro Ser Gly Thr Trp Ser Gly Val Cys Gly
1               5                  10                  15

Asn Asn Asn Ala Cys Lys Asn Gln Cys Ile Asn Leu Glu Lys Ala Arg
                20                  25                  30

His Gly Ser Cys Asn Tyr Val Phe Pro Ala His Lys
            35                  40
```

<210> SEQ ID NO 88
<211> LENGTH: 44
<212> TYPE: PRT
<213> ORGANISM: Artificial Sequence
<220> FEATURE:
<223> OTHER INFORMATION: Lytic Peptide

<400> SEQUENCE: 88

```
Gln Arg Val Cys Asp Lys Pro Ser Gly Thr Trp Ser Gly Leu Cys Gly
1               5                  10                  15

Asn Asn Asn Ala Cys Arg Gln Asn Cys Ile Gln Val Asp Arg Ala Lys
                20                  25                  30

Lys Gly Ser Cys Gln Phe Leu Tyr Pro Ala Lys Lys
            35                  40
```

<210> SEQ ID NO 89
<211> LENGTH: 36
<212> TYPE: PRT
<213> ORGANISM: Artificial Sequence
<220> FEATURE:
<223> OTHER INFORMATION: Lytic Peptide

<400> SEQUENCE: 89

```
Gln Lys Leu Cys Gln Arg Pro Ser Gly Thr Trp Ser Gly Val Cys Gly
1               5                  10                  15

Asn Asn Asn Ala Cys Lys Asn Gln Cys Ile Arg Leu Glu Lys Ala Arg
                20                  25                  30

His Gly Ser Cys
            35
```

<210> SEQ ID NO 90
<211> LENGTH: 36
<212> TYPE: PRT
<213> ORGANISM: Artificial Sequence
<220> FEATURE:
<223> OTHER INFORMATION: Lytic Peptide

<400> SEQUENCE: 90

```
Gln Arg Val Cys Asn Lys Pro Ser Gly Thr Trp Ser Gly Leu Cys Gly
1               5                  10                  15

Asn Asn Asn Ala Cys Arg Gln Asn Cys Ile Lys Val Asp Arg Ala Lys
```

Lys Gly Ser Cys
        35

<210> SEQ ID NO 91
<211> LENGTH: 20
<212> TYPE: PRT
<213> ORGANISM: Artificial Sequence
<220> FEATURE:
<223> OTHER INFORMATION: Lytic Peptide

<400> SEQUENCE: 91

Met Leu Glu Glu Leu Phe Glu Glu Met Thr Glu Phe Ile Glu Glu Val
1               5                   10                  15

Ile Glu Thr Met
        20

<210> SEQ ID NO 92
<211> LENGTH: 1228
<212> TYPE: DNA
<213> ORGANISM: Artificial Sequence
<220> FEATURE:
<223> OTHER INFORMATION: Ubi3 ubiquitin-lytic peptide fusion gene
      construct

<400> SEQUENCE: 92
ccaaagcaca tacttatcga tttaaatttc atcgaagaga ttaatatcga ataatcatat      60
acatacttta aatcataaac aaattttaaa tacatatatc tggtatataa ttaatttttt    120
aaagtcatga agtatgtatc aaatacacat atggaaaaaa ttaactattc ataatttaaa    180
aaatagaaaa gatacatcta gtgaaattag gtgcatgtat caaatacatt aggaaaaggg    240
catatatctt gatctagata attaacgatt ttgatttatg tataatttcc aaatgaaggt    300
ttatatctac ttcagaaata acaatatact tttatcagaa cattcaacaa agcaacaacc    360
aactagagtg aaaaatacac attgttctct agacatacaa aattgagaaa agaatctcaa    420
aatttagaga acaaatctg aatttctaga agaaaaaaat aattatgcac tttgctattg    480
ctcgaaaaat aaatgaaaga attagactt ttttaaaaga tgttagacta gatatactca    540
aaagctatta aaggagtaat attcttctta cattaagtat tttagttaca gtcctgtaat    600
taaagacaca ttttagattg tatctaaact taaatgtatc tagaatacat atatttgaat    660
gcatcatata catgtatccg acacaccaat tctcataaaa aacgtaatat cctaaactaa    720
tttatccttc aagtcaactt aagcccaata tacattttca tctctaaagg cccaagtggc    780
acaaaatgtc aggcccaatt acgaagaaaa gggcttgtaa aacccctaata aagtggcact    840 ggcagagctt acactctcat tccatcaaca aagaaaccct aaaagccgca gcgccactga    900
tttctctcct ccaggcgaag atgcagatct tcgtgaagac ttaacggggg aagacgatca    960
ccctagaggt tgagtcttcc gacaccatcg acaatgtcaa agccaagatc caggacaagg   1020
aagggattcc cccagaccag cagcgtttga ttttcgccgg aaagcagctt gaggatggtc   1080
gtactcttgc cgactacaac atccagaagg agtcaactct ccatctcgtg ctccgtctcc   1140
gtggtggtgg atccgctgtt aaagagtgg gtcgtaggtt gaaaaagttg gaccgtaaga   1200
ttgataggtt aggagttgat ttttgatc                                      1228

<210> SEQ ID NO 93
<211> LENGTH: 1154
<212> TYPE: DNA

<213> ORGANISM: Artificial Sequence
<220> FEATURE:
<223> OTHER INFORMATION: Ubi3-ubiquitin insert sequence

<400> SEQUENCE: 93

| | | | | | |
|---|---|---|---|---|---|
| ccaaagcaca | tacttatcga | tttaaatttc | atcgaagaga | ttaatatcga | ataatcatat | 60 |
| acatacttta | aatacataac | aaattttaaa | tacatatatc | tggtatataa | ttaattttt | 120 |
| aaagtcatga | agtatgtatc | aaatacacat | atggaaaaaa | ttaactattc | ataatttaaa | 180 |
| aaatagaaaa | gatacatcta | gtgaaattag | gtgcatgtat | caaatacatt | aggaaaaggg | 240 |
| catatatctt | gatctagata | attaacgatt | ttgatttatg | tataatttcc | aaatgaaggt | 300 |
| ttatatctac | ttcagaaata | acaatatact | tttatcagaa | cattcaacaa | agcaacaacc | 360 |
| aactagagtg | aaaaatacac | attgttctct | agacatacaa | aattgagaaa | agaatctcaa | 420 |
| aatttagaga | aacaaatctg | aatttctaga | agaaaaaaat | aattatgcac | tttgctattg | 480 |
| ctcgaaaaat | aaatgaaaga | aattagactt | ttttaaaaga | tgttagacta | gatatactca | 540 |
| aaagctatta | aaggagtaat | attcttctta | cattaagtat | tttagttaca | gtcctgtaat | 600 |
| taaagacaca | ttttagattg | tatctaaact | taaatgtatc | tagaatacat | atatttgaat | 660 |
| gcatcatata | catgtatccg | acacaccaat | tctcataaaa | aacgtaatat | cctaaactaa | 720 |
| tttatccttc | aagtcaactt | aagcccaata | tacattttca | tctctaaagg | cccaagtggc | 780 |
| acaaaatgtc | aggcccaatt | acgaagaaaa | gggcttgtaa | aaccctaata | aagtggcact | 840 |
| ggcagagctt | acactctcat | tccatcaaca | aagaaaccct | aaaagccgca | gcgccactga | 900 |
| tttctctcct | ccaggcgaag | atgcagatct | tcgtgaagac | cttaacgggg | aagacgatca | 960 |
| ccctagaggt | tgagtcttcc | gacaccatcg | acaatgtcaa | agccaagatc | caggacaagg | 1020 |
| aagggattcc | cccagaccag | cagcgtttga | ttttcgccgg | aaagcagctt | gaggatggtc | 1080 |
| gtactcttgc | cgactacaac | atccagaagg | agtcaactct | ccatctcgtg | ctccgtctcc | 1140 |
| gtggtggtgg | atcc | | | | | 1154 |

<210> SEQ ID NO 94
<211> LENGTH: 78
<212> TYPE: PRT
<213> ORGANISM: Artificial Sequence
<220> FEATURE:
<223> OTHER INFORMATION: Ubiquitin Polypeptide

<400> SEQUENCE: 94

Met Gln Ile Phe Val Lys Thr Leu Thr Gly Lys Thr Ile Thr Leu Glu
1               5                   10                  15

Val Glu Ser Ser Asp Thr Ile Asp Asn Val Lys Ala Lys Ile Gln Asp
            20                  25                  30

Lys Glu Gly Ile Pro Pro Asp Gln Gln Arg Leu Ile Phe Ala Gly Lys
        35                  40                  45

Gln Leu Glu Asp Gly Arg Thr Leu Ala Asp Tyr Asn Ile Gln Lys Glu
    50                  55                  60

Ser Thr Leu His Leu Val Leu Arg Leu Arg Gly Gly Ser
65                  70                  75

<210> SEQ ID NO 95
<211> LENGTH: 2077
<212> TYPE: DNA
<213> ORGANISM: Artificial Sequence
<220> FEATURE:
<223> OTHER INFORMATION: Ubi7 ubiquitin-lytic peptide fusion gene construct
<210> NAME/KEY: misc_feature
<222> LOCATION: (1)..(2077)
<223> OTHER INFORMATION: "n"= A, T, C, G

<400> SEQUENCE: 95

```
tctacattaa actaatattt gaaatctcaa ttttatgatt ttttaaattc actttatatc      60
caagacaatt tncancttca aaaagtttta ttaaanattt acattagttt tgttgatgag     120
gatgacaaga tnttggtcat caattacata tacccaaatt gaatagtaag caacttcaat     180
gtttttcata atgataatga cagacacaan nnaaacccat ttattattca cattgattga     240
gttttatatg caatatagta ataataataa tatttcttat aaagcaagag gtcaattttt     300
ttttaattat accacgtcac taaattatat ttgataatgt aaaacaattc aaattttact     360
taaatatcat gaaataaact attttttataa ccaaattact aaattttttcc aataaaaaaa     420
agtcattaag aagacataaa ataaatttga ggtaaangag tgaagtcgac tgactttttt     480
ttttttttatc ataagaaaat aaattattaa ctttaaccta ataaaacact aatataattt     540
catggaatct aatacttacc tcttagaaat aagaaaaagt gtttctaata gaccctcaat     600
ttacattaaa tattttcaat caaatttaaa taacaaatat caatatgagg tcaataacaa     660
tatcaaaata atatgaaaaa agagcaaatac ataatataag ggacgattta agtgcgatta     720
tcaaggtagt attatatcct aatttgctaa tatttgngct cttatattta aggtcatgtt     780
catgataaac ttgaaatgcg ctatattaga gcatatatta aataaaaaa atacctaaaa     840
taaaattaag ttattttttag tatatatttt tttacatgac ctacattttt ctgggttttt     900
ctaaaggagc gtgtaagtgt cgacctcatt ctcctaattt tccccaccac ataaaaatta     960
aaaaggaaag gtagcttttg cgtgttgttt tggtacacta cacctcatta ttacacgtgt    1020
cctcatataa ttggttaacc ctatgaggcg gtttcgtcta gagtcggcca tgccatctat    1080
aaaatgaagc tttctgcacc tcattttttt catcttctat ctgatttcta ttataatttc    1140
tctcaattgc cttcaaattt ctctttaagg ttagaatctt ctctattttt ggttttttgta    1200
tgtttagatt ctcgaattag ctaatcaggc gctgttatag ccttcctttt tgagtctctc    1260
ctcggttgtc ttgatggaaa aggcctaaca tttgagtttt tttacgtctg gtttgatgga    1320
aaaggcctac aattggccgt tttccccgtt cgttttgatg aaaaagcccc tagtttgaga    1380
tttttttttct gtcgttcgtt ctaaaggttt aaaattagag ttttttacatt tgtttgatga    1440
aaaaggcctt aaattttgagt ttttccggtt gatttgatga aaaagcccta gaatttgtgt    1500
ttttccgtcg gtttgattct gaaggcctaa aatttgagtt tctccggctg ttttgatgaa    1560
aaagccctaa atttgagttt ctccggctgt tttgatgaaa aagccctaaa tttgaagttt    1620
tttccccgtg ttttagattg tttaggttttt aattctcgaa tcagctaatc agggagtgtg    1680
aaagccctaa attgaagttt ttttcgttgt tctgattgtt gtttttatga atttgcagat    1740
gcagatcttt gtgaaaactc tcaccggaaa gactatcacc ctagaggtgg aaagttctga    1800
tacaatcgac aacgttaagg ctaagatcca ggataaggaa ggaattcccc cggatcagca    1860
aaggcttatc ttcgccggaa agcagttgga ggacggacgt actctagctg attacaacat    1920
ccagaaggag tctaccctcc atttggtgct ccgtctacgt ggaggtggat ccgctgttaa    1980
aagagtgggt cgtaggttga aaaagttgga ccgtaagatt gataggttag gagttgattt    2040
ttgatctaga gtcgaccgat cccccgaatt tccccga                               2077
```

<210> SEQ ID NO 96
<211> LENGTH: 2022

```
<212> TYPE: DNA
<213> ORGANISM: Artificial Sequence
<220> FEATURE:
<223> OTHER INFORMATION: Ubi7-ubiquitin insert sequence
<221> NAME/KEY: misc_feature
<222> LOCATION: (1)..(2022)
<223> OTHER INFORMATION: "n"= A, T, C, G

<400> SEQUENCE: 96
tttatcaatc agatttgaac atataaataa atataaattg tctcaataat tctacattaa      60
actaatattt gaaatctcaa ttttatgatt ttttaaattc actttatatc caagacaatt     120
tncancttca aaaagtttta ttaaanattt acattagttt tgttgatgag gatgacaaga     180
tnttggtcat caattacata tacccaaatt gaatagtaag caacttcaat gttttttcata    240
atgataatga cagacacaan nnaaacccat ttattattca cattgattga gttttatatg     300
caatatagta ataataataa tatttcttat aaagcaagag gtcaatttt ttttaattat      360
accacgtcac taaattatat tgataatgt aaaacaattc aaattttact taaatatcat      420
gaaataaact atttttataa ccaaattact aaattttttcc aataaaaaaa agtcattaag    480
aagacataaa ataaatttga ggtaaangag tgaagtcgac tgactttttt tttttttatc     540
ataagaaaat aaattattaa ctttaaccta ataaaacact aatataattt catggaatct     600
aatacttacc tcttagaaat aagaaaaagt gtttctaata gaccctcaat ttacattaaa     660
tattttcaat caaatttaaa taacaaatat caatatgagg tcaataacaa tatcaaaata     720
atatgaaaaa agagcaatac ataatataag ggacgattta agtgcgatta tcaaggtagt     780
attatatcct aatttgctaa tatttgngct cttatattta aggtcatgtt catgataaac     840
ttgaaatgcg ctatattaga gcatatatta aaataaaaaa atacctaaaa taaaattaag    900
ttattttttag tatatatttt tttacatgac ctacatttt ctgggttttt ctaaaggagc     960
gtgtaagtgt cgacctcatt ctcctaattt tccccaccac ataaaaatta aaaaggaaag    1020
gtagcttttg cgtgttgttt tggtacacta cacctcatta ttacacgtgt cctcatataa    1080
ttggttaacc ctatgaggcg gtttcgtcta gagtcggcca tgccatctat aaaatgaagc    1140
tttctgcacc tcatttttt catcttctat ctgatttcta ttataatttc tctcaattgc     1200
cttcaaattt ctcttaagg ttagaatctt ctctatttt ggttttgta tgtttagatt      1260
ctcgaattag ctaatcaggc gctgttatag cccttccttt tgagtctctc ctcggttgtc    1320
ttgatggaaa aggcctaaca tttgagtttt tttacgtctg gtttgatgga aaaggcctac    1380
aattggccgt tttccccgtt cgttttgatg aaaaagcccc tagtttgaga ttttttttct    1440
gtcgttcgtt ctaaaggttt aaaattagag tttttacatt tgtttgatga aaaaggcctt    1500
aaatttgagt ttttccggtt gatttgatga aaaagcccta gaatttgtgt ttttccgtcg    1560
gtttgattct gaaggcctaa aatttgagtt tctccggctg ttttgatgaa aaagccctaa    1620
atttgagttt ctccggctgt tttgatgaaa agccctaaa tttgaagttt ttccccgtg     1680
ttttagattg tttaggtttt aattctcgaa tcagctaatc agggagtgtg aaagccctaa    1740
attgaagttt ttttcgttgt tctgattgtt gtttttatga atttgcagat gcagatcttt    1800
gtgaaaactc tcaccggaaa gactatcacc ctagaggtgg aaagttctga tacaatcgac    1860
aacgttaagg ctaagatcca ggataaggaa ggaattcccc cggatcagca aaggcttatc    1920
ttcgccggaa agcagttgga ggacggacgt actctagctg attacaacat ccagaaggag    1980
tctacccctcc atttggtgct ccgtctacgt ggaggtggat cc                      2022
```

```
<210> SEQ ID NO 97
<211> LENGTH: 37
<212> TYPE: PRT
<213> ORGANISM: Artificial Sequence
<220> FEATURE:
<223> OTHER INFORMATION: Lytic Peptide

<400> SEQUENCE: 97

Lys Arg Lys Arg Ala Val Lys Arg Val Gly Arg Arg Leu Lys Lys Leu
1               5                   10                  15

Ala Arg Lys Ile Ala Arg Leu Gly Val Ala Lys Leu Ala Gly Leu Arg
            20                  25                  30

Ala Val Leu Lys Phe
        35

<210> SEQ ID NO 98
<211> LENGTH: 23
<212> TYPE: PRT
<213> ORGANISM: Artificial Sequence
<220> FEATURE:
<223> OTHER INFORMATION: Lytic Peptide

<400> SEQUENCE: 98

Ala Val Lys Arg Val Gly Arg Arg Leu Lys Lys Leu Asp Arg Lys Ile
1               5                   10                  15

Asp Arg Leu Gly Val Asp Phe
            20

<210> SEQ ID NO 99
<211> LENGTH: 101
<212> TYPE: PRT
<213> ORGANISM: Artificial Sequence
<220> FEATURE:
<223> OTHER INFORMATION: Ubiquitin-Lytic Peptide

<400> SEQUENCE: 99

Met Gln Ile Phe Val Lys Thr Leu Thr Gly Lys Thr Ile Thr Leu Glu
1               5                   10                  15

Val Glu Ser Ser Asp Thr Ile Asp Asn Val Lys Ala Lys Ile Gln Asp
            20                  25                  30

Lys Glu Gly Ile Pro Pro Asp Gln Gln Arg Leu Ile Phe Ala Gly Lys
        35                  40                  45

Gln Leu Glu Asp Gly Arg Thr Leu Ala Asp Tyr Asn Ile Gln Lys Glu
    50                  55                  60

Ser Thr Leu His Leu Val Leu Arg Leu Arg Gly Gly Ser Ala Val
65                  70                  75                  80

Lys Arg Val Gly Arg Arg Leu Lys Lys Leu Asp Arg Lys Ile Asp Arg
                85                  90                  95

Leu Gly Val Asp Phe
            100

<210> SEQ ID NO 100
<211> LENGTH: 78
<212> TYPE: PRT
<213> ORGANISM: Artificial Sequence
<220> FEATURE:
<223> OTHER INFORMATION: Ubiquitin Polypeptide

<400> SEQUENCE: 100

Met Gln Ile Phe Val Lys Thr Leu Thr Gly Lys Thr Ile Thr Leu Glu
1               5                   10                  15

Val Glu Ser Ser Asp Thr Ile Asp Asn Val Lys Ala Lys Ile Gln Asp
```

-continued

```
                20                  25                  30
Lys Glu Gly Ile Pro Pro Asp Gln Gln Arg Leu Ile Phe Ala Gly Lys
        35                  40                  45

Gln Leu Glu Asp Gly Arg Thr Leu Ala Asp Tyr Asn Ile Gln Lys Glu
    50                  55                  60

Ser Thr Leu His Leu Val Leu Arg Leu Arg Gly Gly Ser
65                  70                  75
```

<210> SEQ ID NO 101
<211> LENGTH: 101
<212> TYPE: PRT
<213> ORGANISM: Artificial Sequence
<220> FEATURE:
<223> OTHER INFORMATION: Ubiquitin-Lytic Peptide

<400> SEQUENCE: 101

```
Met Gln Ile Phe Val Lys Thr Leu Thr Gly Lys Thr Ile Thr Leu Glu
1               5                   10                  15

Val Glu Ser Ser Asp Thr Ile Asp Asn Val Lys Ala Lys Ile Glu Asp
            20                  25                  30

Lys Glu Gly Ile Pro Pro Asp Gln Gln Arg Leu Ile Phe Ala Gly Lys
        35                  40                  45

Gln Leu Glu Asp Gly Arg Thr Leu Ala Asp Tyr Asn Ile Gln Lys Glu
    50                  55                  60

Ser Thr Leu His Leu Val Leu Arg Leu Arg Gly Gly Ser Ala Val
65                  70                  75                  80

Lys Arg Val Gly Arg Arg Leu Lys Lys Leu Asp Arg Lys Ile Asp Arg
                85                  90                  95

Leu Gly Val Asp Phe
            100
```

<210> SEQ ID NO 102
<211> LENGTH: 78
<212> TYPE: PRT
<213> ORGANISM: Artificial Sequence
<220> FEATURE:
<223> OTHER INFORMATION: Ubiquitin Polypeptide

<400> SEQUENCE: 102

```
Met Gln Ile Phe Val Lys Thr Leu Thr Gly Lys Thr Ile Thr Leu Glu
1               5                   10                  15

Val Glu Ser Ser Asp Thr Ile Asp Asn Val Lys Ala Lys Ile Glu Asp
            20                  25                  30

Lys Glu Gly Ile Pro Pro Asp Gln Gln Arg Leu Ile Phe Ala Gly Lys
        35                  40                  45

Gln Leu Glu Asp Gly Arg Thr Leu Ala Asp Tyr Asn Ile Gln Lys Glu
    50                  55                  60

Ser Thr Leu His Leu Val Leu Arg Leu Arg Gly Gly Ser
65                  70                  75
```

UBIQUITIN-LYTIC PEPTIDE GENE PROMOTER

CROSS REFERENCE TO RELATED APPLICATIONS

This application is a continuation of application Ser. No. 08/801,028, filed Feb. 19, 1997, now U.S. Pat. No. 6,018,102, which is a continuation of application Ser. No. 08/279,472, filed Jul. 22, 1994 now abandoned.

BACKGROUND OF THE INVENTION

1. Field of the Invention

The present invention relates to ubiquitin-lytic peptide fusion gene constructs with enhanced stability and gene expression, ubiquitin-lytic peptide fusion protein products, and methods of making and using the same.

2. Description of Related Art

Naturally occurring lytic peptides play an important if not critical role as immunological agents in insects and have some, albeit secondary, defense functions in a range of other animals. The function of these peptides is to destroy procaryotic and other non-host cells by disrupting the cell membrane and promoting cell lysis. Common features of these naturally occurring lytic peptides include an overall basic charge, a small size (23–39 amino acid residues), and the ability to form amphipathic α-helices or β-pleated sheets. Several types of lytic peptides have been identified: cecropins (described in U.S. Pat. Nos. 4,355,104 and 4,520,016 to Hultmark et al.), defensins, sarcotoxins, melittin, and magainins (described in U.S. Pat. No. 4,810,777 to Zasloff). Each of these peptide types is distinguished by sequence and secondary structure characteristics.

Several hypotheses have been suggested for the mechanism of action of the lytic peptides: disruption of the membrane lipid bilayer by the amphipathic α-helix portion of the lytic peptide; lytic peptide formation of ion channels, which results in osmotically induced cytolysis; lytic peptide promotion of protein aggregation, which results in ion channel formation; and lytic peptide-induced release of phospholipids. Whatever the mechanism of lytic peptide-induced membrane damage, an ordered secondary conformation such as an amphipathic α-helix and positive charge density are features that appear to participate in the function of the lytic peptides.

Active synthetic analogs of naturally occurring lytic peptides have been produced and tested in vitro against a variety of prokaryotic and eukaryotic cell types (see for example Arrowood, M. J., et al., J. Protozool. 38: 161s [1991]; Jaynes, J. M., et al., FASEB J. 2: 2878 [19881]), including: gram positive and gram negative bacteria, fungi, yeast, protozoa, envelope viruses, virus-infected eukaryotic cells, and neoplastic or transformed mammalian cells. The results from these studies indicate that many of the synthetic lytic peptide analogs have similar or higher levels of lytic activity for many different types of cells, compared to the naturally occurring forms. In addition, the peptide concentration required to lyse microbial pathogens such as protozoans, yeast, and bacteria does not lyse normal mammalian cells. However, because previous work demonstrates that absolute sequence is not important as long as positive charge and amphipathy are preserved, the level of activity for a given synthetic peptide is difficult to predict.

The specificity of the lytic action also depends upon the concentration of the peptide and the type of membrane with which it interacts. Jaynes, J. M. et al., Peptide Research 2: 157 (1989) discuss the altered cytoskeletal characteristics of transformed or neoplastic mammalian cells that make them susceptible to lysis by the peptides. In these experiments, normal, human non-transformed cells remained unaffected at a given peptide concentration while transformed cells were lysed; however, when normal cells were treated with the cytoskeletal inhibitors cytochalasin D or colchicine, sensitivity to lysis increased. The experiments show that the action of lytic peptides on normal mammalian cells is limited. This resistance to lysis was most probably due to the well-developed cytoskeletal network of normal cells. In contrast, transformed cell lines which have well-known cytoskeletal deficiencies were sensitive to lysis. Because of differences in cellular sensitivity to lysis, lytic peptide concentration can be manipulated to effect lysis of one cell type but not another at the same locus.

Synthetic lytic peptide analogs can also act as agents of eukaryotic cell proliferation. Peptides that promote lysis of transformed cells will, at lower concentrations, promote cell proliferation in some cell types. This stimulatory activity is thought to depend on the channel-forming capability of the peptides, which somehow stimulates nutrient uptake, calcium influx or metabolite release, thereby stimulating cell proliferation (see Jaynes, J. M., Drug News & Perspectives 3: 69 [1990]; and Reed, W. A. et al., Molecular Reproduction and Development 31: 106 [1992]). Thus, at a given concentration, these peptides stimulate or create channels that can be beneficial to the normal mammalian cell in a benign environment where it is not important to exclude toxic compounds.

The synthetic lytic peptide analogs typically contain as few as 12 and as many as 40 amino acid residues. A phenylalanine residue is often positioned at the amino terminus of the protein to provide an aromatic moiety analogous to the tryptophan residue located near the amino terminus of natural cecropins and a UV-absorbing moiety with which to monitor the purification of the synthetic peptide. The basis for the design of these lytic peptide analogs is that a peptide of minimal length, having an amphipathic α-helical structural or a β-pleated sheet motif, and overall positive charge density effects lytic activity.

Plant disease is one of the leading causes of crop loss in the world and is estimated to cause up to one third of total crop loss worldwide; for example, in the potato losses associated with bacterial disease are as high as 25% of worldwide production. Additionally, the cultivation of a few species of plants in a concentrated area exacerbates the spread of disease. Recent advances in genetic engineering have lead to the development of plants with disease resistant phenotypes based on the expression of recombinant DNA molecules. Transgenic tobacco plants were engineered with both a wound inducible PiII promoter and a constitutive 35S promoter to express two lytic peptides (SHIVA-1 and SB-37) with bacteriolytic activity. The SHIVA-1 plant demonstrated enhanced resistance to bacterial wilt caused by infection by *Pseudomonas solanacearum* (Jaynes, J. M., et al., Plant Science 89: 43 (1993); Destefano-Beltran, L., et al., Biotechnology in Plant Disease Control, pp. 175–189, Wiley-Liss (1993). Thus lytic peptides have valuable uses as anti-phytopathogenic agents. However, chemical synthesis of these lytic peptides is very expensive. Therefore, alternate, more economical and efficient methods of synthesis are needed, such as in vivo synthesis in host cells using recombinant DNA methods.

Recombinant DNA molecules are produced by subcloning genes into plasmids using a bacterial host intermediate. In principle this technique is straightforward. However, any sequence that interferes with bacterial growth through replication or production of products toxic to the bacteria, such a lytic peptides, are difficult to clone. Often, host bacterial cells containing mutated forms of the DNA sequences encoding toxic products will be selected. These mutations can result in either decreased expression or production of an inactive product. Bacteria will even insert mutations that prevent expression of a potentially toxic product in cloned genes controlled by a eukaryotic promoter that is not active in prokaryotes. The effect of this selection of mutated species leads to an inability to isolate sub-clones containing a non-mutated gene of choice. Thus, some sub-cloned genes are unstable in their bacterial hosts, although this instability can only be shown empirically. The bacteriolytic activity of the lytic peptides is an obstacle to the production of stable recombinant DNA molecules that express the genes at high levels.

For example, in an attempt to sub-clone into a standard plasmid vector a gene coding for frog magainin, a natural lytic peptide, bacterial transformants contained deletion mutations in the magainin coding region. Another attempt was made to sub-clone a synthetic lytic peptide (SEQ ID NO. 98) into a standard plasmid vector (pUC19) containing the Cauliflower Mosaic Virus 35S promoter. The resulting transformants were screened by polymerase chain reaction (PCR). However, out of 30 colonies, only 2 sub-clones gave faint positive signals. These two sub-clones were sequenced. The sequence showed that one clone had a point mutation that introduced a stop codon ¾ of the way through the lytic peptide, and the other clone had a point mutation that changed the start codon from methionine to isoleucine. Both mutations would prevent the biosynthesis of the protein. Four more clones were analyzed, and of these four, one was sub-cloned in the wrong orientation, and three others had mutations introduced into the sequence. One of these sub-clones was selected for further analysis, but it inhibited the growth of its E. coil host. Thus, the production of recombinant DNA molecules coding for lytic peptides is difficult due to the uncertainty in obtaining the correct sub-clone.

Ubiquitin is a small, highly conserved protein present in all eukaryotes. Ubiquitins are encoded by gene families that are characterized by two types of basic structures. Polyubiquitin genes contain several direct repeats of ubiquitin, and ubiquitin-ribosomal fusion genes encode a single ubiquitin unit fused to the coding region for a small ribosomal associated protein. Both of these gene types are translated as polyproteins and then are processed by an endogenous ubiquitin hydrolase present in eukaryotes to release multiple ubiquitin proteins or ubiquitin and the ribosomal associated protein. A number of ubiquitin cDNAs or genomic clones have been isolated, including plant ubiquitin cDNAs and genomic clones from the potato (Garbarino, J. and Belknap, W., Plant Molecular Biology 24: 119 (1994); Garbarino. J. et al., Plant Molecular Biology 20: 235 (1992)).

U.S. Pat. Nos. 5,093,242 and 5,132,213 to Bachmair et al. teach the use of a ubiquitin cloning vector as a method of producing specified protein amino-termini. A recombinant DNA molecule was constructed with a protein coding gene fused at its amino terminus to a ubiquitin coding gene. Due to translation as a polypeptide and cleavage by hydrolases, a protein with any amino acid at the amino terminus can be generated. The amino terminus can be used to control the metabolic stability of the protein. However, the metabolic stability of the protein is dependent on the resulting amino acid at the amino-terminus, not the generation of a translation polypeptide.

The forgoing facts suggest that although lytic peptides as a class may include species that are efficacious in destroying bacteria, neoplastic cells, fungi, virus-infected cells, and protozoa, this lytic characteristic also decreases the stability of sub-cloned lytic peptides in host cells. This decreased stability hinders efforts co develop a more economical and efficient means of synthesizing lytic peptides.

It would therefore be a significant advance in the art, and is correspondingly an object of the present invention to develop a method of sub-cloning nucleotide sequences coding for lytic peptides into expression vectors, providing gene constructs with enhanced stability and gene expression and reduced toxicity.

SUMMARY OF THE INVENTION

The present invention relates generally to ubiquitin-lytic peptide fusion nucleic acid expression vectors comprising a promoter and ubiquitin polypeptide coding sequence ligated to a lytic peptide, ubiquitin-lytic peptide fusion protein products, and methods of making and using the same, as hereinafter more fully described.

It is another object of the invention to provide ubiquitin-lytic peptide fusion expression vectors and protein products derived therefrom.

It is another object of the invention to provide ubiquitin-lytic peptide fusion expression vectors that are expressed in plants having utility for promoting wound healing and combatting bacterial infections in plants.

It is a further object of this invention to provide ubiquitin-lytic peptide fusion polypeptides having utility for combatting protozoal infections, neoplasias, fungal infections, viral infections, and bacterial infections in mammals and plants.

It is yet another object of this invention to develop a method of sub-cloning polypeptide sequences in ubiquitin-fusion expression vectors with enhanced stability and gene expression.

It is yet another object of this invention to provide expression vectors containing constitutive and wound inducible ubiquitin promoters that are expressed in eukaryotic cells.

It is yet another object of this invention to provide expression vectors with prokaryotic promoters that express ubiquitin-lytic peptide fusion genes in prokaryotic hosts, the products of which can be cleaved in vitro by ubiquitin hydrolases.

These and other objects and advantages will be more fully apparent from the ensuing disclosure and claims.

DETAILED DESCRIPTION OF THE INVENTION AND PREFERRED EMBODIMENTS THEREOF

Figure 1:
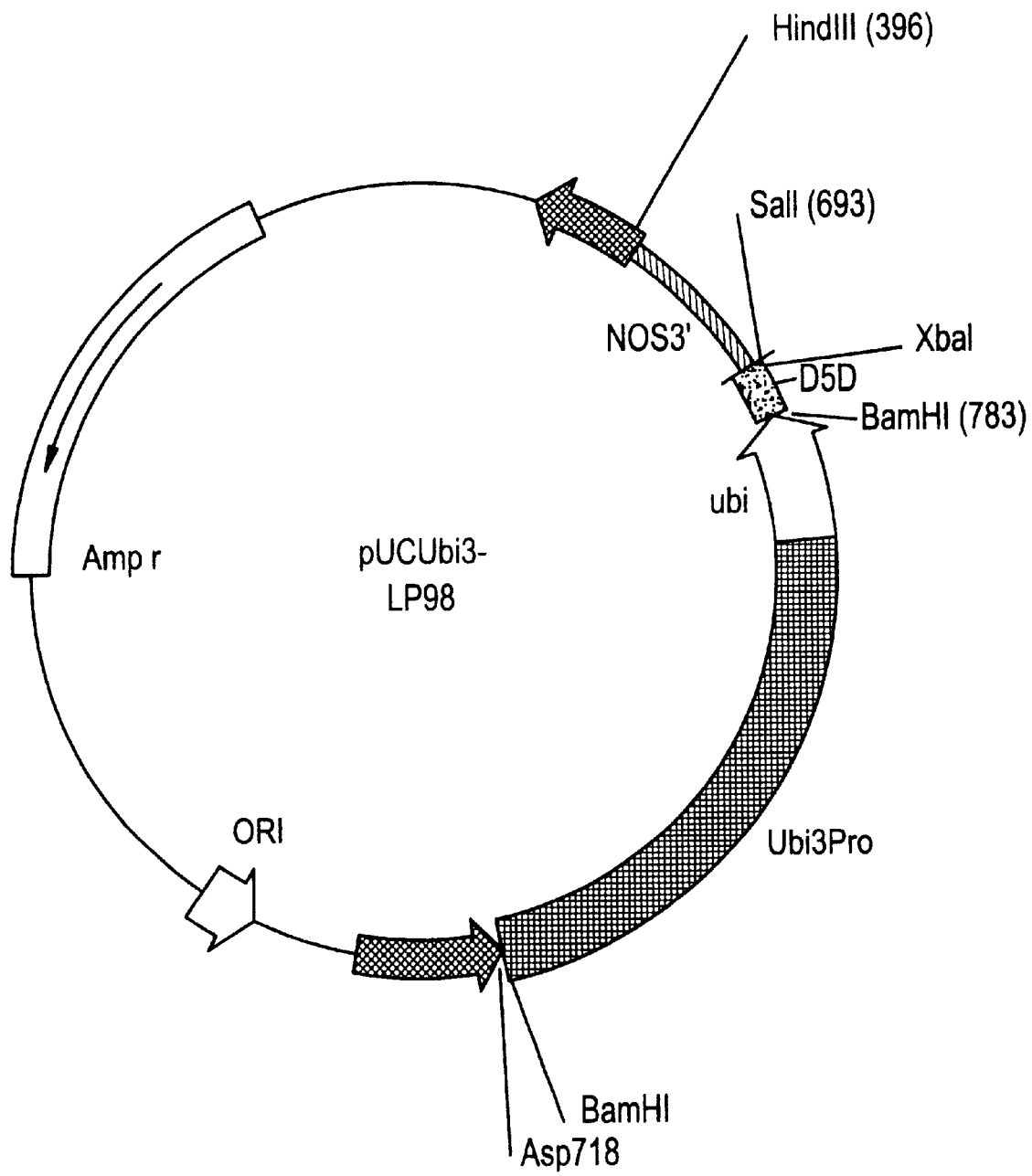
FIG. 1 is a map of a recombinant nucleic acid expression vector pUCUbi3-LP98 containing a 920 bp ubiquitin-ribosomal fusion gene promoter region linked to a 228 bp coding region for a ubiquitin polypeptide with a six bp BamHI site at the 3' end (SEQ ID NO. 93) that is fused at its 3' end to a gene coding for a lytic peptide (D5D*, SEQ ID NO. 98). The Ubi3 ubiquitin-lytic peptide nucleotide sequence corresponds to SEQ ID NO. 92. A nopaline synthase polyadenylation signal is located at the 3' end of the lytic peptide gene.

The disclosures of prior co-pending U.S. patent application Ser. No. 08/039,620 filed Jun. 4, 1993 in the names of Jesse M. Jaynes and Gordon R. Julian, U.S. patent application Ser. No. 08/148,889 filed Nov. 8, 1993 in the name of Gordon R. Julian, U.S. patent application Ser. No. 08/148,491 filed Nov. 8, 1993 in the name of Gordon R. Julian, U.S. patent application Ser. No. 08/225,476 filed Apr. 8, 1994 in the names of Jesse M. Jaynes and Gordon R. Julian, and U.S. patent application Ser. No. 08/231,730 filed Apr. 20, 1994 in the names of Jesse M. Jaynes and Gordon R. Julian, are all hereby incorporated herein by reference in their entirety.

The term "amphipathic" as used herein refers to the distribution of hydrophobic and hydrophilic amino acid residues along opposing faces of α-helix structure or other secondary conformation, which results in one face of the α-helix structure being predominantly hydrophobic and the other face being predominantly hydrophilic. The degree of amphipathy of a peptide can be assessed by plotting the sequential amino acid residues on an Edmunson helical wheel (see also Kamtekar, S. et al., Science 262: 1680 (1993).

The terms "peptidel" and "polypeptide" as used herein refer to a molecule composed of a chain of amino acid residues and is intended to be construed as inclusive of polypeptides and peptides per se having molecular weights of up to 10,000 daltons, as well as proteins having molecular weights of greater that about 10,000 daltons, wherein the molecular weights are number average molecular weights. The term is also intended to be construed as inclusive of functional equivalents thereof when used in reference to a specific peptide coding sequence in the specification and claims herein. Functional equivalents of peptides and polypeptides include but are not limited to deletions, additions, and substitutions of amino acids in the polypeptide or peptide chain that do not adversely affect the overall function of the resulting peptide or polypeptide.

The term "plasmid" as used herein refers to a DNA molecule that is capable of autonomous replication within a host cell, either extrachromosomally or as part of the host cell chromosome(s). The starting plasmids herein are commercially available, are publicly available on an unrestricted basis, or can be constructed from such available plasmids as disclosed herein and/or in accordance with published procedures. In certain instances, as will be apparent to the ordinarily skilled artisan, other plasmids known in the art may be used interchangeable with plasmids described herein.

The term "ligation" as used herein refers to the process of forming phosphodiester bonds between two double-stranded DNA fragments. Unless otherwise specified, ligation is accomplished using standard procedures known to one skilled in the art.

The term "polymerase chain reaction," or "PCR" as used herein refers to a method for amplification of a desired nucleotide sequence in vitro, as described in U.S. Pat. No. 4,683,195, herein incorporated by reference in its entirety.

The term "nucleic acid" as used herein refers to deoxyribonucleic acid molecules (DNA) composed of a chain of deoxyribonucleotides and ribonucleic acid molecules (RNA) composed of a chain of ribonucleotides. The term "nucleic acid" as used herein is to be construed as including functional equivalents thereof when used in reference to a specific nucleotide sequence in the specification and claims herein. Functional equivalents of nucleic acid molecules include synonymous coding sequences with one or more codon substitutions and deletions or additions that do not effect the overall function of the resulting nucleic acid molecule. The degeneracy of the genetic code is well known to the art; therefore, synonymous coding sequences with one or more codon substitutions can be readily determined by one of ordinary skill in the art. Synonymous nucleotide coding sequences vary from the exemplified coding sequences but encode proteins of the same amino acid sequences as those specifically provided herein or proteins with similar function and are therefore also regarded as functional equivalents thereof.

The term "promoter" as used herein refers to an untranslated (i.e. one that does not result in a peptide or protein product) sequence upstream of the polypeptide coding region of a nucleotide sequence that controls transcription of a gene. Promoters typically fall into two classes, constitutive and inducible. Inducible promoters initiate high levels of transcription of the nucleic acid under their control in response to external stimuli. Constitutive promoters maintain a relatively constant level of transcription in a given cell. Suitable promoters for use in the present may include both prokaryotic and eukaryotic promoters, with all ubiquitin promoters being preferred, solanaceous plant ubiquitin promoters being highly preferred, and potato ubiquitin promoters being most preferred. Additional control sequences such as ribosomal binding sites and enhancers may be included as control sequences when necessary.

The term "polyadenylation site" as used herein refers to a control sequence located on the 3' end of a gene construct that provides a signal for cleavage and polyadenylation of the transcription unit expressed from the promoter. These control sequences are known to one skilled in the art The term "expression" as used herein refers to transcription and/or translation of a nucleic acid sequence coding for a protein or peptide.

In one embodiment, the present invention is directed to an isolated nucleotide sequence comprising a gene coding for a ubiquitin polypeptide and functional equivalents thereof, linked to a ubiquitin promoter and functional equivalents thereof. Suitable ubiquitin promoters for use in the present invention include, but are not limited to, ubiquitin promoters from solanaceous plants. Preferably, the ubiquitin promoter is a potato plant ubiquitin promoter and most preferably it is the potato Ubi3 or Ubi7 promoter. In embodiments wherein the isolated nucleotide sequence codes for the potato Ubi3 promoter linked to a gene coding for a ubiquitin polypeptide it has a nucleotide sequence according to SEQ ID NO. 93. The Ubi3 promoter alone also has utility as constitutive promoter in eukaryotes, In embodiments wherein the isolated nucleocide sequence codes for the potato Ubi7 promoter linked to a gene coding for a ubiquitin polypeptide it has a nucleotide sequence according to SEQ ID NO. 96. The Ubi7 nucleotide sequence according to SEQ ID No. 96 includes an intron that is part of the ubiquitin transcription unit. The intron is not required for gene expression from the Ubi7 promoter, thus the Ubi7 promoter region without the intron can be considered as a specific functional equivalent of the Ubi7 promoter. The Ubi7 promoter alone, with or without the intron, has utility as a wound inducible promoter in eukaryotes.

Preferably, the nucleotide sequence comprising the isolated ubiquitin promoter and gene coding for a ubiquitin polypeptide further comprises a gene coding for a lytic peptide ligated to the 3' end of the gene coding for a ubiquitin polypeptide. Suitable genes coding for a lytic peptide have a nucleotide sequence coding for any one of the amino acid sequences according to SEQ ID NO. 1–91 and 97–98.

In one preferred embodiment, the present invention is directed to an isolated nucleotide sequence comprising a gene coding for a lytic peptide ligated to the 3' end of the gene coding for a ubiquitin polypeptide linked to the Ubi3 ubiquitin promoter having a nucleotide sequence according to SEQ ID NO. 92. In an alternative of this embodiment, the present invention is directed to an isolated nucleotide sequence comprising a gene coding for a lytic peptide ligated to the 3' end of the gene coding for a ubiquitin polypeptide linked to a Ubi7 ubiquitin promoter having a nucleotide sequence according to SEQ ID NO. 95.

In another embodiment, the present invention is directed to a recombinant nucleic acid expression vector. The vector is characterized in that it comprises a nucleotide sequence wherein a gene coding for a ubiquitin polypeptide is linked to a ubiquitin promocer. Preferably, the present invention is directed to a recombinant nucleic acid expression vector characterized in that it further comprises a nucleotide sequence wherein a gene coding for a lytic peptide is ligated to the 3' end of the gene coding for a ubiquitin polypeptide linked to a ubiquitin promoter. Suitable vectors for use in this invention include any eukaryotic or prokaryotic expression vectors known in the art. Preferable vectors for use in this invention are pUCl9 and pCGN1547.

In another embodiment, the present invention is directed to a host cell that is transformed by a recombinant DNA expression vector comprising a gene coding for a ubiquitin polypeptide linked to a ubiquitin promoter. Suitable host cells for transformation in the present invention include all known bacterial host cells, with all strains of Escherichia coli and Agrobacterium tumeraciens being preferred. Preferably, the present invention is directed to a host cell the recombinant DNA expression vector further comprises a gene coding for a lytic peptide ligated to the 3' end of the gene coding for a ubiquitin polypeptide linked to a ubiquitin promoter. Suitable genes coding for a lytic peptide have a nucleotide sequence coding for any one of the amino acid sequences according to SEQ ID NO. 1–91 and 97–98.

Preferably, the present invention is directed to a solanaceous plant host cell that is transformed by a recombinant DNA expression vector. Most preferably the solanaceous plant cell is a potato plant host cell.

In another embodiment, the present invention is directed to an isolated nucleotide sequence and functional equivalents thereof coding for a lytic peptide, where the nucleotide sequence has a sequence coding for any one of the amino acid sequences according to SEQ ID NO. 1–91 and 97–98.

In yet another embodiment, the present invention is directed to a purified ubiquitin polypeptide and functional equivalents thereof having an amino acid sequence according to SEQ ID NO. 94. This embodiment can further comprise a lytic peptide translationally fused to the carboxy terminus of a ubiquitin polypeptide.

In another embodiment, the present invention is directed to a method of sub-clonlng nucleotide sequences coding for lytic peptides and expressing such sequences in cells. The method comprises a first step wherein a recombinant nucleic acid containing a gene coding for a lytic peptide ligated to a gene coding for a ubiquitin polypeptide linked to a ubiquitin promoter is produced in a first host cell. Suitable first host cells include any known bacterial host cells. Preferably, the first host cell is either an Escherichia coli cell or an Agrobacterium tumefaciens cell.

If the peptides are sub-cloned using such a ubiquitin-fusion expression vector, the following advantage results: the lytic peptide gene constructs have increased stability in the bacterial host. While not wishing to be bound by any one theory, the present inventors believe that the stability is due to the ubiquitin protein coding nucleic acid region fused to the 5' end of the lytic peptide nucleic acid sequence. Bacteria do not contain the endogenous hydrolase necessary for cleavage of the ubiquitin fusion protein, so the gene constructs are not toxic to bacteria, since active lytic peptide cannot released. Thus functional equivalents of the ubiquitin fusion polypeptide include any ubiquitin molecule that is capable of deceiving the host cell into viewing the gene construct and its products as non-toxic.

In a variation of this embodiment, the recombinant nucleic acid vector is isolated from the first host cell and expressed in a second host cell. Suitable second host cells are plant and animal cells, preferably a solanaceous plant cell, and most preferably a potato plant cell. In the second host cell the fusion gene is expressed at high levels and the polyprotein is cleaved by endogenous ubiquitin hydrolases to produce active lytic peptide. These transgenic hosts provide from the expression vector lytic peptides in vivo to combat bacterial infections, fungal infections, protozoal infections, virus infections, and neoplasias. In addition, expression vectors containing ubiquitin promoters that are either constitutive or wound inducible are used to express peptides in eukaryotes.

The present invention is also directed to a method of sub-cloning nucleotide sequences coding for lytic peptides and expressing such sequences in cells. The method comprises producing in a host cell a recombinant nucleic acid expression vector comprising a gene coding for a lytic peptide ligated to the 3' end of a gene coding for a ubiquitin promoter linked to a prokaryotic promoter sequence. Suitable prokaryotic promoters include those known to one skilled in the art to be active in prokaryotes and used in plasmid vectors for bacterial gene expression.

The recombinant nucleic acid expression vector is expressed in the host cell and ubiquitin-lytic peptide fusion polypeptides are isolated from the host. Preferably, the host cell is either an Escherichia coli cell or an Agrobacterium tumefaciens cell. The isolated ubiquitin-lytic peptide fusion polypeptides are then cleaved in vitro by ubiquitin hydrolases to release the lytic peptides from the ubiquitin polypeptide (see U.S. Pat. No. 5,196,321 to Bachmair et al.). The active lytic peptides are then used to treat bacterial infections, fungal infections, protozoal infections, virus infections, and neoplasias. These isolated lytic peptides are in some instances glyoxylated or methylated in vitro to stabilize against proteolytic digestion in vivo.

Ubiquitin fusion expression vectors thus have broad utility as cloning and expression vectors to stabilize and sub-clone lytic peptides nucleotide sequences, as well as a wide variety of protein coding nucleic acid sequences that are otherwise toxic to their hosts. The ubiquitin-lytic peptide expression vectors also have broad utility as an economical and efficient means to synthesize lytic peptides in host cells. These lytic peptides have utility for combatting protozoal infections, neoplasias, fungal infections, viral infections, and bacterial infections in mammals and plants.

The features and advantages of the invention are more fully shown by the following illustrative examples and embodiments, which are not to be limitingly construed as regard the broad scope, utility, and applicability of the invention.

EXAMPLE 1

Representative Lytic Peptides and Ubiquitin Polypeptide

Set out in Table 1 below as illustrative examples of lytic peptides are the amino acid sequences of families of related lytic peptides. These lytic peptides are designated for ease of reference as SEQ ID NO. 1–91 and 97–98. Nucleic acid sequences coding for these lytic peptides and functional equivalents thereof represent examples of lytic peptide nucleic acid sequences that are sub-cloned to make ubiquitin-lytic peptide fusion gene constructs and polypeptides. The ubiquitin polypeptide, designated for ease of reference as SEQ ID NO. 94, and functional equivalents thereof, represents an example of the 5' fusion ubiquitin polypeptide.

TABLE 1

LYTIC PEPTIDE SEQUENCES

SEQ ID NO. 1
Phe Ala Val Ala Val Lys Ala Val Lys Lys Ala Val Lys Lys Val Lys
 1               5                  10                 15
Lys Ala Val Lys Lys Ala Val Lys Lys Lys
              20                  25

SEQ ID NO. 2
Phe Ala Val Ala Val Lys Ala Val Ala Val Lys Ala Val Lys Lys Ala
 1               5                  10                 15
Val Lys Lys Val Lys Ala Val Lys Ala Val Lys Lys Lys
              20                  25                 30

SEQ ID NO. 3
Phe Ala Val Ala Val Lys Ala Val Ala Val Lys Ala Val Ala Val Lys
 1               5                  10                 15
Ala Val Lys Lys Ala Val Lys Lys Val Lys Lys Ala Val Lys Lys Ala
              20                  25                 30
Val Lys Lys Lys
       35

SEQ ID NO. 4
Phe Ala Val Ala Val Lys Ala Val Lys Lys Ala Val Lys Lys Val Lys
 1               5                  10                 15
Lys Ala Val Lys Lys Ala Val
              20

SEQ ID NO. 5
Phe Ala Val Ala Val Lys Ala Val Ala Val Lys Ala Val Lys Lys Ala
 1               5                  10                 15
Val Lys Lys Val Lys Lys Ala Val Lys Lys Ala Val
              20                  25

SEQ ID NO. 6
Phe Ala Val Ala Val Lys Ala Val Ala Val Lys Ala Val Ala Val Lys
 1               5                  10                 15
Ala Val Lys Lys Ala Val Lys Lys Val Lys Lys Ala Val Lys Lys Ala
              20                  25                 30
Val

SEQ ID NO. 7
Phe Ala Val Gly Leu Arg Ala Ile Lys Arg Ala Leu Lys Lys Leu Arg
 1               5                  10                 15
Arg Gly Val Arg Lys Val Ala Lys Arg Lys Arg
              20                  25

SEO ID NO. 8
Phe Ala Val Gly Leu Arg Ala Ile Lys Arg Ala Leu Lys Lys Leu Arg
 1               5                  10                 15
Arg Gly Val Arg Lys Val Ala
              20

SEQ ID NO. 9
Lys Arg Lys Arg Ala Val Lys Arg Val Gly Arg Arg Leu Lys Lys Leu
 1               5                  10                 15
Ala Arg Lys Ile Ala Arg Leu Gly Val Ala Phe
              20                  25

SEQ ID NO. 10
Ala Val Lys Arg Val Gly Arg Arg Leu Lys Lys Leu Ala Arg Lys Ile
 1               5                  10                 15
Ala Arg Leu Gly Val Ala Phe
              20

SEQ ID NO. 11
Phe Ala Val Gly Leu Arg Ala Ile Lys Arg Ala Leu Lys Lys Leu Arg
 1               5                  10                 15
Arg Gly Val Arg Lys Val Ala Lys Arg Lys Arg Lys Lys Asp Leu
              20                  25                 30

SEQ ID NO. 12
Phe Ala Val Gly Leu Arg Ala Ile Lys Arg Ala Leu Lys Lys Leu Arg
 1               5                  10                 15
Arg Gly Val Arg Lys Val Ala Lys Asp Leu
              20                  25

SEQ ID NO. 13
Lys Arg Lys Arg Ala Val Lys Arg Val Gly Arg Arg Leu Lys Lys Leu

TABLE 1-continued

LYTIC PEPTIDE SEQUENCES

```
 1               5                  10                 15
Ala Arg Lys Ile Ala Arg Leu Gly Val Ala Phe Lys Asp Leu
                20                 25                 30

SEQ ID NO. 14
Ala Val Lys Arg Val Gly Arg Arg Leu Lys Lys Leu Ala Arg Lys Ile
 1               5                  10                 15
Ala Arg Leu Gly Val Ala Phe Lys Asp Leu
                20                 25

SEQ ID NO. 15
Lys Lys Lys Lys Phe Val Lys Val Ala Lys Val Lys Lys Val
 1               5                  10                 15
Ala Lys Lys Val Ala Lys Val Ala Val Ala Val
                20                 25

SEQ ID NO. 16
Lys Lys Lys Lys Phe Val Lys Val Ala Lys Val Lys Lys Val
 1               5                  10                 15
Ala Lys Lys Val Ala Lys Val Ala Val Ala Lys Val Ala Val
                20                 25                 30

SEQ ID NO. 17
Lys Lys Lys Lys Phe Val Lys Val Ala Lys Val Lys Lys Val
 1               5                  10                 15
Ala Lys Lys Val Ala Lys Val Ala Ala Lys Val Ala Val Ala Lys
                20                 25                 30
Val Ala Val Ala Val
         35

SEQ ID NO. 18
Phe Val Lys Lys Val Ala Lys Lys Val Lys Val Ala Lys Lys Val
 1               5                  10                 15
Ala Lys Val Ala Val Ala Val
                20

SEQ ID NO. 19
Phe Val Lys Lys Val Ala Lys Lys Val Lys Val Ala Lys Lys Val
 1               5                  10                 15
Ala Lys Val Ala Val Ala Lys Val Ala Val Ala Val
                20                 25

SEQ ID NO. 20
Phe Val Lys Lys Val Ala Lys Lys Val Lys Val Ala Lys Lys Val
 1               5                  10                 15
Ala Lys Val Ala Val Ala Lys Val Ala Val Ala Lys Val Ala Val Ala
                20                 25                 30
Val

SEQ ID NO. 21
Lys Lys Lys Lys Phe Val Lys Val Ala Lys Val Ala Lys Lys Val
 1               5                  10                 15
Ala Lys Val Ala Lys Lys Val Ala Lys Lys Val
                20                 25

SEQ ID NO. 22
Lys Lys Lys Lys Phe Val Lys Val Ala Lys Val Ala Lys Lys Val
 1               5                  10                 15
Ala Lys Val Ala Lys Lys Val Ala Lys Val Ala Lys Lys Val Ala
                20                 25                 30

SEQ ID NO. 23
Lys Lys Lys Lys Phe Val Lys Val Ala Lys Val Ala Lys Lys Val
 1               5                  10                 15
Ala Lys Val Ala Lys Lys Val Ala Lys Val Ala Lys Lys Val Ala
                20                 25                 30
Lys Val Ala Lys Lys
         35

SEQ ID NO. 24
Phe Val Lys Lys Val Ala Lys Val Ala Lys Lys Val Ala Lys Val Ala
 1               5                  10                 15
Lys Lys Val Ala Lys Lys Val
                20

SEQ ID NO. 25
Phe Val Lys Lys Val Ala Lys Val Ala Lys Lys Val Ala Lys Val Ala
```

TABLE 1-continued

LYTIC PEPTIDE SEQUENCES

```
 1             5              10             15
Lys Lys Val Ala Lys Lys Val Ala Lys Lys Val Ala
            20             25
```

SEQ ID NO. 26
```
Phe Val Lys Lys Val Ala Lys Val Ala Lys Lys Val Ala Lys Val Ala
 1             5              10             15
Lys Lys Val Ala Lys Lys Val Ala Lys Lys Val Ala Lys Val Ala Lys
            20             25             30
Lys
```

SEQ ID NO. 27
```
Phe Val Lys Lys Val Ala Lys Val Ala Lys Lys Val Ala Lys Val Ala
 1             5              10             15
Lys Lys Val Ala Lys Lys Val Lys Lys Lys
            20             25
```

SEQ ID NO 28
```
Phe Val Lys Lys Val Ala Lys Val Ala Lys Lys Val Ala Lys Val Ala
 1             5              10             15
Lys Lys Val Ala Lys Lys Val Ala Lys Lys Val Ala Lys Lys Lys Lys
            20             25             30
```

SEQ ID NO. 29
```
Phe Val Lys Lys Val Ala Lys Val Ala Lys Lys Val Ala Lys Val Ala
 1             5              10             15
Lys Lys Val Ala Lys Lys Val Ala Lys Lys Val Ala Lys Val Ala Lys
            20             25             30
Lys Lys Lys Lys Lys
            35
```

SEQ ID NO. 30
```
Phe Lys Val Lys Ala Lys Val Lys Ala Lys Val Lys Lys Lys Lys
 1             5              10             15
```

SEQ ID NO. 31
```
Phe Lys Val Lys Ala Lys Val Lys Ala Lys Val Lys Ala Lys Val Lys
 1             5              10             15
Ala Lys Lys Lys
            20
```

SEQ ID NO. 32
```
Phe Lys Val Lys Ala Lys Val Lys Ala Lys Val Lys Ala Lys Val Lys
 1             5              10             15
Ala Lys Val Lys Ala Lys Val Lys Lys Lys
            20             25
```

SEQ ID NO. 33
```
Phe Lys Val Lys Ala Lys Val Lys Ala Lys Val Lys
 1             5              10
```

SEQ ID NO. 34
```
Phe Lys Val Lys Ala Lys Val Lys Ala Lys Val Lys Ala Lys Val Lys
 1             5              10             15
Ala
```

SEQ ID NO. 35
```
Phe Lys Val Lys Ala Lys Val Lys Ala Lys Val Lys Ala Lys Val Lys
 1             5              10             15
Ala Lys Val Lys Ala Lys Val
            20
```

SEQ ID NO. 36
```
Lys Lys Lys Phe Lys Val Lys Ala Lys Val Lys Ala Lys Val Lys
 1             5              10             15
```

SEQ ID NO. 37
```
Lys Lys Lys Phe Lys Val Lys Ala Lys Val Lys Ala Lys Val Lys
 1             5              10             15
Ala Lys Val Lys Ala
            20
```

SEQ ID NO. 38
```
Lys Lys Lys Lys Phe Lys Val Lys Ala Lys Val Lys Ala Lys Val Lys
 1             5              10             15
Ala Lys Val Lys Ala Ly Val Lys Ala Lys Val
            20             25
```

TABLE 1-continued

LYTIC PEPTIDE SEQUENCES

SEQ ID NO. 39
Phe Lys Lys Val Lys Lys Val Ala Lys Lys Val Cys Lys Cys Val Lys
1               5                   10                  15
Lys Ala Val Lys Lys Val Lys Lys Phe
            20                  25

SEQ ID NO. 40
Phe Ala Val Ala Val Lys Ala Val Lys Lys Ala Val Lys Lys Val Lys
1               5                   10                  15
Lys Ala Val Lys Lys Ala Val Cys Cys Cys Cys
            20                  25

SEQ ID NO. 41
Cys Cys Cys Cys Phe Val Lys Lys Val Ala Lys Lys Val Lys Lys Val
1               5                   10                  15
Ala Lys Lys Val Ala Lys Val Ala Val Ala Val
            20                  25

SEQ ID NO. 42
Phe Ala Val Ala Val Lys Ala Val Lys Lys Ala Val Lys Lys Val Lys
1               5                   10                  15
Lys Ala Val Lys Lys Ala Val Ser Ser Ser Ser
            20                  25

SEQ ID NO. 43
Ser Ser Ser Ser Phe Val Lys Lys Val Ala Lys Lys Val Lys Lys Val
1               5                   10                  15
Ala Lys Lys Val Ala Lys Val Ala Val Ala Val
            20                  25

SEQ ID NO. 44
Phe Ala Leu Ala Leu Lys Ala Leu Lys Lys Ala Leu Lys Lys Leu Lys
1               5                   10                  15
Lys Ala Leu Lys Lys Ala Leu
            20

SEQ ID NO 45
Leu Ala Lys Lys Leu Ala Lys Lys Leu Lys Lys Leu Ala Lys Lys Leu
1               5                   10                  15
Ala Lys Leu Ala Leu Ala Phe
            20

SEQ ID NO. 46
Phe Ala Phe Ala Phe Lys Ala Phe Lys Lys Ala Phe Lys Lys Phe Lys
1               5                   10                  15
Lys Ala Phe Lys Lys Ala Phe
            20

SEQ ID NO. 47
Phe Ala Ile Ala Ile Lys Ala Ile Lys Lys Ala Ile Lys Lys Ile Lys
1               5                   10                  15
Lys Ala Ile Lys Lys Ala Ile
            20

SEQ ID NO. 48
Phe Ala Lys Lys Phe Ala Lys Lys Phe Lys Lys Phe Ala Lys Lys Phe
1               5                   10                  15
Ala Lys Phe Ala Phe Ala Phe
            20

SEQ ID NO. 49
Phe Lys Arg Leu Ala Lys Ile Lys Val Leu Arg Leu Ala Lys Ile Lys
1               5                   10                  15
Arg

SEQ ID NO. 50
Lys Leu Lys Leu Ala Val Lys Leu Val Gly Leu Leu Arg Lys Lys Arg
1               5                   10                  15
Ala Leu Lys Ile Ala Leu Arg Gly Val Ala Lys Arg Ala Gly Arg Leu
            20                  25                  30
Ala Val Arg Lys Phe
        35

SEQ ID NO. 51
Phe Ala Arg Ala Arg Lys Ala Arg Lys Lys Ala Arg Lys Lys Arg Lys
1               5                   10                  15

TABLE 1-continued

LYTIC PEPTIDE SEQUENCES

Lys Ala Arg Lys Ala Arg Lys Asp Arg
            20              25

SEQ ID NO. 52
Phe Ala Val Ala Val Cys Ala Val Cys Cys Ala Val Cys Cys Val Cys
1               5                   10                  15
Cys Ala Val Cys Cys Ala Val
            20

SEQ ID NO. 53
Phe Ala Val Ala Val Ser Ala Val Ser Ser Ala Val Ser Ser Val Ser
1               5                   10                  15
Ser Ala Val Ser Ser Ala Val
            20

SEQ ID NO. 54
Phe Ala Val Ala Val Ser Ala Val Ser Ser Ala Val Ser Ser Val Ser
1               5                   10                  15
Ser Ala Val Ser Ser Ala Val Ser Ser Ser Ser
            20              25

SEQ ID NO. 55
Phe Ala Lys Lys Phe Ala Lys Lys Phe Lys Lys Phe Ala Lys Lys Phe
1               5                   10                  15
Ala Lys Phe Ala Phe Ala Phe Lys Lys Lys Lys
            20              25

SEQ ID NO. 56
Lys Lys Lys Lys Phe Ala Lys Lys Phe Ala Lys Lys Phe Lys Lys Phe
1               5                   10                  15
Ala Lys Lys Phe Ala Lys Phe Ala Phe Ala Phe
            20              25

SEQ ID NO. 57
Phe Ala Arg Lys Phe Leu Lys Arg Phe Lys Lys Phe Val Arg Lys Phe
1               5                   10                  15
Ile Arg Phe Ala Phe Leu Phe
            20

SEQ ID NO.58
Phe Ala Arg Lys Phe Leu Lys Arg Phe Lys Lys Phe Val Arg Lys Phe
1               5                   10                  15
Ile Arg Phe Ala Phe Leu Phe Lys Arg Lys Arg
            20              25

SEQ ID NO. 59
Lys Arg Lys Arg Phe Ala Arg Lys Phe Leu Lys Arg Phe Lys Lys Phe
1               5                   10                  15
Val Arg Lys Phe Ile Arg Phe Ala Phe Leu Phe
            20              25

SEQ ID NO. 60
Ile Ala Lys Lys Ile Ala Lys Lys Ile Lys Lys Ile Ala Lys Lys Ile
1               5                   10                  15
Ala Lys Ile Ala Ile Ala Ile
            20

SEQ ID NO. 61
Ile Ala Lys Lys Ile Ala Lys Lys Ile Lys Lys Ile Ala Lys Lys Ile
1               5                   10                  15
Ala Lys Ile Ala Ile Ala Ile Lys Lys Lys Lys
            20              25

SEQ ID NO. 62
Lys Lys Lys Lys Ile Ala Lys Lys Ile Ala Lys Lys Ile Lys Lys Ile
1               5                   10                  15
Ala Lys Lys Ile Ala Lys Ile Ala Ile Ala Ile
            20              25

SEQ ID NO. 63
Ile Ala Arg Lys Ile Leu Lys Arg Ile Lys Lys Ile Val Arg Lys Phe
1               5                   10                  15
Ile Arg Ile Ala Ile Leu Ile
            20

SEQ ID NO. 64
Ile Ala Arg Lys Ile Leu Lys Arg Ile Lys Lys Ile Val Arg Lys Phe

TABLE 1-continued

LYTIC PEPTIDE SEQUENCES

```
               1           5              10             15
            Ile Arg Ile Ala Ile Leu Ile Lys Arg Lys Arg
                    20              25

SEQ ID NO. 65
Lys Arg Lys Arg Ile Ala Arg Lys Ile Leu Lys Arg Ile Lys Lys Ile
 1               5                  10                  15
Val Arg Lys Phe Ile Arg Ile Ala Ile Leu Ile
            20              25

SEQ ID NO. 66
Phe Lys Leu Arg Ala Lys Ile Lys Val Arg Leu Arg Ala Lys Ile Lys
 1               5                  10                  15
Leu

SEQ ID NO. 67
Lys Arg Lys Arg Phe Lys Leu Arg Ala Lys Ile Lys Val Arg Leu Arg
 1               5                  10                  15
Ala Lys Ile Lys Leu
            20

SEQ ID NO. 68
Phe Lys Leu Arg Ala Lys Ile Lys Val Arg Leu Arg Ala Lys Ile Lys
 1               5                  10                  15
Leu Lys Arg Lys Arg
            20

SEQ ID NO. 69
Phe Lys Leu Arg Ala Lys Ile Lys Val Arg Leu Arg Ala Lys Ile Lys
 1               5                  10                  15
Leu Arg Val Lys Leu Lys Ile
            20

SEQ ID NO. 70
Phe Lys Leu Arg Ala Lys Ile Lys Val Arg Leu Arg Ala Lys Ile Lys
 1               5                  10                  15
Leu Arg Val Lys Leu Lys Ile Lys Arg Lys Arg
            20              25

SEQ ID NO. 71
Lys Arg Lys Arg Phe Lys Leu Arg Ala Lys Ile Lys Val Arg Leu Arg
 1               5                  10                  15
Ala Lys Ile Lys Leu Arg Val Lys Leu Lys Ile
            20              25
SEQ ID NO. 72
Phe Lys Leu Arg Ala Lys Ile Lys Val Arg Leu Arg Ala Lys Ile Lys
 1               5                  10                  15
Leu Arg Val Lys Leu Lys Ile Arg Ala Arg Ile Lys Leu
            20              25

SEQ ID NO. 73
Phe Lys Leu Arg Ala Lys Ile Lys Val Arg Leu Arg Ala Lys Ile Lys
 1               5                  10                  15
Leu Arg Val Lys Leu Lys Ile Arg Ala Arg Ile Lys Leu Lys Arg Lys
            20              25              30
Arg

SEQ ID NO. 74
Lys Arg Lys Arg Phe Lys Leu Arg Ala Lys Ile Lys Val Arg Leu Arg
 1               5                  10                  15
Ala Lys Ile Lys Leu Arg Val Lys Leu Lys Ile Arg Ala Arg Ile Lys
            20              25              30
Leu

SEQ ID NO. 75
Phe Lys Leu Arg Ala Lys Ile Lys Val Arg Leu Arg Ala Lys Ile Lys
 1               5                  10                  15
Leu Val Phe Ala Ile Leu Leu
            20

SEQ ID NO.76
Phe Lys Leu Arg Ala Lys Ile Lys Val Arg Leu Arg Ala Lys Ile Lys
 1               5                  10                  15
Leu Val Phe Ala Ile Leu Leu Lys Arg Lys Arg
            20              25

SEQ ID NO. 77
```

TABLE 1-continued

LYTIC PEPTIDE SEQUENCES

Lys Arg Lys Arg Phe Lys Leu Arg Ala Lys Ile Lys Val Arg Leu Arg
1               5                   10                  15
Ala Lys Ile Lys Leu Val Phe Ala Ile Leu Leu
            20                  25

SEQ ID NO. 78
Val Phe Ala Ile Leu Leu Phe Lys Leu Arg Ala Lys Ile Lys Val Arg
1               5                   10                  15
Leu Arg Ala Lys Ile Lys Leu
            20

SEQ ID NO. 79
Val Phe Ala Ile Leu Leu Phe Lys Leu Arg Ala Lys Ile Lys Val Arg
1               5                   10                  15
Leu Arg Ala Lys Ile Lys Leu Lys Arg Lys Arg
            20                  25

SEQ ID NO. 80
Lys Arg Lys Arg Val Phe Ala Ile Leu Leu Phe Lys Leu Arg Ala Lys
1               5                   10                  15
Ile Lys Val Arg Leu Arg Ala Lys Ile Lys Leu
            20                  25

SEQ ID NO. 81
Val Gly Gly Cys Val Arg Gly Arg Cys Pro Ser Gly Met Cys Cys Ser
1               5                   10                  15
Gln Phe Gly Tyr Cys Gly Lys Gly Pro Lys Tyr Cys Gly
            20                  25

SEQ ID NO. 82
Val Gly Glu Cys Val Arg Gly Arg Cys Pro Ser Gly Met Cys Cys Ser
1               5                   10                  15
Gln Phe Gly Tyr Cys Gly Lys Gly Pro Lys Tyr Cys Gly Arg
            20                  25                  30

SEQ ID NO. 83
Leu Gly Asp Cys Leu Lys Gly Lys Cys Pro Ser Gly Met Cys Cys Ser
1               5                   10                  15
Asn Tyr Gly Phe Cys Gly Arg Gly Pro Arg Phe Cys Gly Lys
            20                  25                  30

SEQ ID NO. 84
Gln Cys Ile Gly Asn Gly Gly Arg Cys Asn Glu Asn Val Gly Pro Pro
1               5                   10                  15
Tyr Cys Cys Ser Gly Phe Cys Leu Arg Gln Pro Gly Gln Gly Tyr Gly
            20                  25                  30
Tyr Cys Lys Asn Arg
            35

SEQ ID NO. 85
Cys Ile Gly Asn Gly Gly Arg Cys Asn Glu Asn Val Gly Pro Pro Tyr
1               5                   10                  15
Cys Cys Ser Gly Phe Cys Leu Arg Gln Pro Asn Gln Gly Tyr Gly Val
            20                  25                  30
Cys Arg Asn Arg
            35

SEQ ID NO. 86
Cys Ile Gly Gln Gly Gly Lys Cys Gln Asp Gln Leu Gly Pro Pro Phe
1               5                   10                  15
Cys Cys Ser Gly Tyr Cys Val Lys Asn Pro Gln Asn Gly Phe Gly Leu
            20                  25                  30
Cys Lys Gln Lys
            35

SEQ ID NO. 87
Gln Lys Leu Cys Glu Arg Pro Ser Gly Thr Trp Ser Gly Val Cys Gly
1               5                   10                  15
Asn Asn Asn Ala Cys Lys Asn Gln Cys Ile Asn Leu Glu Lys Ala Arg
            20                  25                  30
His Gly Ser Cys Asn Tyr Val Phe Pro Ala His Lys
            35                  40

SEQ ID NO. 88
Gln Arg Val Cys Asp Lys Pro Ser Gly Thr Trp Ser Gly Leu Cys Gly
1               5                   10                  15
Asn Asn Asn Ala Cys Arg Gln Asn Cys Ile Gln Val Asp Arg Ala Lys

TABLE 1-continued

LYTIC PEPTIDE SEQUENCES

```
                  20                    25                    30
Lys Gly Ser Cys Gln Phe Leu Tyr Pro Ala Lys Lys
            35                    40

SEQ ID NO. 89
Gln Lys Leu Cys Gln Arg Pro Ser Gly Thr Trp Ser Gly Val Cys Gly
 1               5                   10                  15
Asn Asn Asn Ala Cys Lys Asn Gln Cys Ile Arg Leu Glu Lys Ala Arg
            20                  25                  30
His Gly Ser Cys
            35

SEQ ID NO. 90
Gln Arg Val Cys Asn Lys Pro Ser Gly Thr Trp Ser Gly Leu Cys Gly
 1               5                   10                  15
Asn Asn Asn Ala Cys Arg Gln Asn Cys Ile Lys Val Asp Arg Ala Lys
            20                  25                  30
Lys Gly Ser Cys
            35

SEQ ID NO. 91
Met Leu Glu Glu Leu Phe Glu Glu Met Thr Glu Phe Ile Glu Glu Val
 1               5                   10                  15
Ile Glu Thr Met
            20

SEQ ID NO. 94
Met Gln Ile Phe Val Lys Thr Leu
 1               5
Thr Gly Lys Thr Ile Thr Leu Glu Val Glu Ser Ser Asp Thr
    10                  15                  20
Ile Asp Asn Val Lys Ala Lys Ile Gln Asp Lys Glu Gly Ile
        25                  30                      35
Pro Pro Asp Gln Gln Arg Leu Ile Phe Ala Gly Lys Gln Leu
            40                  45                  50
Glu Asp Gly Arg Thr Leu Ala Asp Tyr Asn Ile Gln Lys Glu
                55                  60
Ser Thr Leu His Leu Val Leu Arg Leu Arg Gly Gly Gly Ser
65                  70                  75

SEQ ID NO. 97
Lys Arg Lys Arg Ala Val Lys Arg Val Gly Arg Arg Leu Lys Lys Leu
 1               5                   10                  15
Ala Arg Lys Ile Ala Arg Leu Gly Val Ala Lys Leu Ala Gly Leu Arg
            20                  25                  30
Ala Val Leu Lys Phe
            35

SEQ ID NO. 98
Ala Val Lys Arg Val Gly Arg Arg Leu Lys Lys Leu Asp Arg Lys Ile
 1               5                   10                  15
Asp Arg Leu Gly Val Asp Phe
            20
```

EXAMPLE 2

Construction of Ubiquitin-lytic Peptide Fusion Plasmids with Ubiquitin-ribosomal Fusion Gene Promoter (Ubi3)

Exemplary and preferred pUC19 and pCGN1547 plasmid vectors containing a potato (*Solanum tuberosum*) ubiquitin-ribosomal fusion promoter (Ubi3), a region coding for a ubiquitin polypeptide, and a gene coding for a lytic peptide are constructed.

To obtain the genomic clone containing a ubiquitin-ribosomal fusion promoter and ubiquitin polypeptide coding region, a λFIXII potato genomic library is first prescreened using PCR. The PCR primers are homologous to regions of the ubiquitin-ribosomal fusion cDNA (see Garbarino J., et al., Plant Molecular Biology 20: 235 (1992); Garbarino J. and Belknap W., Plant Molecular Biology 24: 119 (1994); both of which are hereby incorporated by reference herein in their entirety). A primer 5' to the beginning ATG of ubiquitin and a primer complementary to a sequence near the 5' end of the ribosomal protein are used.

The library is plated in 22 aliquots containing approximately $0.5 \times 10^6$ pfu (plaque forming units) each on an *E. coli* lawn. A plug is taken from each of the 22 resulting plaques and the eluant from each is subjected to PCR under standard conditions. The PCR products are run on agarose gels. The gels are then blotted and probed with the ubiquitin coding region of the ubiquitin-ribosomal fusion cDNA according to standard conditions. Two of the plugs produce PCR products that hybridize to the cDNA probe. Both of these are the correct size for the predicted ubiquitin-ribosomal fusion genomic fragment.

The eluants from these two plugs are then plated and screened with the ubiquitin coding region of the ubiquitin-ribosomal fusion cDNA according to standard conditions. For verification, the positive plaques from the initial screen are replated and screened with a probe containing both the ribosomal protein-coding region and the 3' end of the potato ubiquitin-ribosomal fusion cDNA.

The genomic clones are sequenced using Sequenase version 2.0 (United States Biochemical Corporation) or Promega fmol DNA Sequencing System using standard conditions. A genomic clone containing both the ubiquitin-ribosomal fusion promoter region and the ubiquitin-ribosomal fusion coding region is identified.

A chimeric gene is then constructed with a portion of the potato ubiquitin-ribosomal fusion genomic clone ligated to a lytic peptide gene. PCR is used to generate the Ubi3 promoter and ubiquitin portion of the chimeric gene. The Ubi3 promoter region includes the 920 bp promoter region upstream of the ubiquitin ATG, and the ubiquitin polypeptide coding region is 228 bp plus 6 bp of a BamHI restriction site at the 3' end (SEQ ID No. 93). The primers contain BamHI restriction sites and are homologous to the 5' end of the Ubi3 promoter and to the 3' end of the ubiquitin polypeptide coding region. The ubiquitin-ribosomal fusion genomic clone is used as the amplification template. This insert is first sub-cloned into The plasmid pCGN1547, as described in Garbarino et al., Plant Molecular Biology 24: 119 (1994). The Ubi3 insert is then isolated from pCGN1547 using the BamHI sites and ligated into pUC19 under standard conditions. Transformation of E. coli is done according to standard conditions and correct sub-clones are confirmed by mini-prep or PCR DNA analysis. This plasmid is designated pUCUbi3.

A nucleotide fragment coding for the lytic peptide (corresponding to the amino acid sequence SEQ ID NO. 98) is synthesized using a nucleic acid synthesizer, adding a stop codon to the 3' end, and used as a PCR template. The 5' PCR primer homologous to the lytic peptide nucleotide sequence contains a BamHI site, and the 3' primer contains an XbaI site. These sites are used to sub-clone the PCR generated insert into pUC19. A nopaline synthase polyadenylation signal (NOS3') is then cloned 3' to the lytic peptide sequence. Following sequence analysis, the BamrHI insert containing the Ubi3 promoter and ubiquitin coding region (SEQ ID NO. 93) is cloned 5' to the lytic peptide.

After transforming E. coli under standard conditions, pUC19 sub-clones are selected for mini-prep or PCR DNA analysis according to standard conditions. The direction of the promoter is confirmed and the junction sequences are verified by sequencing according to standard conditions. The resulting Ubi3 ubiquitin-lytic peptide fusion gene construct corresponds to SEQ ID NO. 92. Unlike previous cloning attempts using the CaMV35S promoter, as described in the Background section, the sequence does not reveal any point mutations in the lytic peptide sub-clones. The plasmid is stable in the E. coli host and did not inhibit its growth.

The resulting pUC19 recombinant plasmid is shown in the plasmid map in FIG. 1. The sequence for the Ubi3-ubiquitin insert containing the ubiquitin-ribosomal fusion gene promoter and the ubiquitin coding region corresponds to SEQ ID NO. 93 in Table 2 below. The sequence for the chimeric Ubi3 ubiquitin-lytic peptide fusion gene construct corresponds to SEQ ID NO. 92 in Table 2 below. This plasmid is designated as pUCUbi3-LP98.

The entire Ubi3 ubiquitin-lytic peptide fusion gene construct, including the polyadenylation site, was isolated from pUCl9 as an Asp718/HindIII restriction fragment and sub-cloned into the pCGN1547 Agrobacterium vector for use in plant transformation (see McBride, et al., Plant Molecular Biology 14: 269 (1990). This plasmid is designated as pCGNUbi3-LP98.

TABLE 2

NUCLEOTIDE SEQUENCE OF POTATO UBIQUITIN-RIBOSOMAL FUSION PROMOTER (UBI3) AND UBIQUITIN CODING REGION INSERT, AND UBIQUITIN-
LYTIC PEPTIDE FUSION CONSTRUCT

SEQ ID NO. 92

| | | | | |
|---|---|---|---|---|
| CCAAAGCACA | TACTTATCGA | TTTAAATTTC | ATCGAAGAGA | TTAATATCGA   50 |
| ATAATCATAT | ACATACTTTA | AATACATAAC | AAATTTTAAA | TACATATATC  100 |
| TGGTATATAA | TTAATTTTTT | AAAGTCATGA | AGTATGTATC | AAATACACAT  150 |
| ATGGAAAAAA | TTAACTATTC | ATAATTTAAA | AAATAGAAAA | GATACATCTA  200 |
| GTGAAATTAG | GTGCATGTAT | CAAATACATT | AGGAAAAGGG | CATATATCTT  250 |
| GATCTAGATA | ATTAACGATT | TTGATTTATG | TATAATTTCC | AAATGAAGGT  300 |
| TTATATCTAC | TTCAGAAATA | ACAATATACT | TTTATCAGAA | CATTCAACAA  350 |
| AGCAACAACC | AACTAGAGTG | AAAAATACAC | ATTGTTCTCT | AGACATACAA  400 |
| AATTGAGAAA | AGAATCTCAA | AATTTAGAGA | AACAAATCTG | AATTTCTAGA  450 |
| AGAAAAAAAT | AATTATGCAC | TTTGCTATTG | CTCGAAAAAT | AAATGAAAGA  500 |
| AATTAGACTT | TTTTAAAAGA | TGTTAGACTA | GATATACTCA | AAAGCTATTA  550 |
| AAGGAGTAAT | ATTCTTCTTA | CATTAAGTAT | TTTAGTTACA | GTCCTGTAAT  600 |
| TAAAGACACA | TTTTAGATTG | TATCTAAACT | TAAATGTATC | TAGAATACAT  650 |
| ATATTTGAAT | GCATCATATA | CATGTATCCG | ACACACCAAT | TCTCATAAAA  700 |
| AACGTAATAT | CCTAAACTAA | TTTATCCTTC | AAGTCAACTT | AAGCCCAATA  750 |
| TACATTTTCA | TCTCTAAAGG | CCCAAGTGGC | ACAAAATGTC | AGGCCCAATT  800 |
| ACGAAGAAAA | GGGCTTGTAA | AACCCTAATA | AAGTGGCACT | GGCAGAGCTT  850 |

TABLE 2-continued

NUCLEOTIDE SEQUENCE OF POTATO UBIQUITIN-RIBOSOMAL FUSION
PROMOTER (UBI3) AND UBIQUITIN CODING REGION INSERT, AND
UBIQUITIN-
LYTIC PEPTIDE FUSION CONSTRUCT

```
ACACTCTCAT TCCATCAACA AAGAAACCCT AAAAGCCGCA GCGCCACTGA    900
TTTCTCTCCT CCAGGCGAAG ATG CAG ATC TTC GTG AAG ACC TTA    944
ACG GGG AAG ACG ATC ACC CTA GAG GTT GAG TCT TCC GAC ACC  986
ATC GAC AAT GTC AAA GCC AAG ATC CAG GAC AAG GAA GGG ATT 1028
CCC CCA GAC CAG CAG CGT TTG ATT TTC GCC GGA AAG CAG CTT 1070
GAG GAT GGT CGT ACT CTT GCC GAC TAC AAC ATC CAG AAG GAG 1112
TCA ACT CTC CAT CTC GTG CTC CGT CTC CGT GGT GGT        1148
GGA TCC GCT GTT AAA AGA GTG GGT CGT AGG TTG AAA AAG TTG 1190
GAC CGT AAG ATT GAT AGG TTA GGA GTT GAT TTT TGATC        1228

SEQ ID NO. 99
Met Gln Ile phe Val Lys Thr Leu
1               5

Thr Gly Lys Thr Ile Thr Leu Glu Val Glu Ser Ser Asp Thr
    10              15                  20

Ile Asp Asn Val Lys Ala Lys Ile Gln Asp Lys Glu Gly Ile
        25                  30                  35

Pro Pro Asp Gln Gln Arg Leu Ile Phe Ala Gly Lys Gln Leu
            40                  45                  50

Glu Asp Gly Arg Thr Leu Ala Asp Tyr Asn Ile Gln Lys Glu
                55                  60

Ser Thr Leu His Leu Val Leu Arg Leu Arg Gly Gly
65                  70                  75

Gly Ser Ala Val Lys Arg Val Gly Arg Arg Leu Lys Lys Leu
            80                  85                  90

Asp Arg Lys Ile Asp Arg Leu Gly Val Asp Phe
                95                  100

SEQ ID NO. 93
CCAAAGCACA TACTTATCGA TTTAAATTTC ATCGAAGAGA TTAATATCGA    50
ATAATCATAT ACATACTTTA AATACATAAC AAATTTTAAA TACATATATC   100
TGGTATATAA TTAATTTTTT AAAGTCATGA AGTATGTATC AAATACACAT   150
ATGGAAAAAA TTAACTATTC ATAATTTAAA AAATAGAAAA GATACATCTA   200
GTGAAATTAG GTGCATGTAT CAAATACATT AGGAAAAGGG CATATATCTT   250
GATCTAGATA ATTAACGATT TTGATTTATG TATAATTTCC AAATGAAGGT   300
TTATATCTAC TTCAGAAATA ACAATATACT TTTATCAGAA CATTCAACAA   350
AGCAACAACC AACTAGAGTG AAAAATACAC ATTGTTCTCT AGACATACAA   400
AATTGAGAAA AGAATCTCAA AATTTAGAGA AACAAATCTG AATTTCTAGA   450
AGAAAAAAAT AATTATGCAC TTTGCTATTG CTCGAAAAAT AAATGAAAGA   500
AATTAGACTT TTTTAAAAGA TGTTAGACTA GATATACTCA AAAGCTATTA   550
AAGGAGTAAT ATTCTTCTTA CATTAAGTAT TTTAGTTACA GTCCTGTAAT   600
TAAAGACACA TTTTAGATTG TATCTAAACT TAAATGTATC TAGAATACAT   650
ATATTTGAAT GCATCATATA CATGTATCCG ACACACCAAT TCTCATAAAA   700
```

TABLE 2-continued

NUCLEOTIDE SEQUENCE OF POTATO UBIQUITIN-RIBOSOMAL FUSION
PROMOTER (UBI3) AND UBIQUITIN CODING REGION INSERT, AND
UBIQUITIN-
LYTIC PEPTIDE FUSION CONSTRUCT

```
AACGTAATAT CCTAAACTAA TTTATCCTTC AAGTCAACTT AAGCCCAATA    750

TACATTTTCA TCTCTAAAGG CCCAAGTGGC ACAAAATGTC AGGCCCAATT    800

ACGAAGAAAA GGGCTTGTAA AACCCTAATA AAGTGGCACT GGCAGAGCTT    850

ACACTCTCAT TCCATCAACA AAGAAACCCT AAAAGCCGCA GCGCCACTGA    900

TTTCTCTCCT CCAGGCGAAG ATG CAG ATC TTC GTG AAG ACC TTA    944

ACG GGG AAG ACG ATC ACC CTA GAG GTT GAG TCT TCC GAC ACC  986

ATC GAC AAT GTC AAA GCC AAG ATC CAG GAC AAG GAA GGG ATT 1028

CCC CCA GAC CAG CAG CGT TTG ATT TTC GCC GGA AAG CAG CTT 1070

GAG GAT GGT CGT ACT CTT GCC GAC TAC AAC ATC CAG AAG GAG 1112

TCA ACT CTC CAT CTC GTG CTC CGT CTC CGT GGT GGT GGA TCC 1154
```

SEQ ID NO. 100

```
Met Gln Ile phe Val Lys Thr Leu
1               5

Thr Gly Lys Thr Ile Thr Leu Glu Val Glu Ser Ser Asp Thr
    10              15                  20

Ile Asp Asn Val Lys Ala Lys Ile Gln Asp Lys Glu Gly Ile
        25              30                      35

Pro Pro Asp Gln Gln Arg Leu Ile Phe Ala Gly Lys Gln Leu
            40              45                      50

Glu Asp Gly Arg Thr Leu Ala Asp Tyr Asn Ile Gln Lys Glu
                55              60

Ser Thr Leu His Leu Val Leu Arg Leu Arg Gly Gly Gly Ser
65              70              75
```

EXAMPLE 3
Construction of Ubiquitin-Lytic Peptide Fusion Plasmids with Polyubiquitin Promoter and Intron (Ubi7)

Exemplary and preferred pUC19 and pCGN1547 plasmid vectors containing a potato (*Solanum tuberosum*) polyubiquitin promoter and intron (Ubi7), a region coding for a ubiquitin polypeptide, and a gene coding for a lytic peptide are constructed.

To obtain the genomic clone containing a polyubiquitin promoter, intron and ubiquitin polypeptide coding region, a λFIXII potato genomic library was first prescreened using PCR as described in Example 2 above. The PCR primers are homologous to regions of the polyubiquitin cDNA (see Garbarino J., et al., Plant Molecular Biology 20: 235 (1992)). A primer homologous to the 5' untranslated region of ubiquitin in the polyubiquitin cDNA and a primer complementary to the amino terminus of the ubiquitin coding region in the polyubiquitin cDNA are used. A genomic clone containing both the polyubiquitin promoter region, intron, and the polyubiquitin coding region was identified.

A chimeric gene is then constructed with a portion of the potato polyubiquitin genomic clone ligated to a lytic peptide gene, as described in Example 2. PCR is used to generate the Ubi7-ubiquitin portion of the chimeric gene. The Ubi7 promoter region includes the 1220 bp promoter and 568 bp intron upstream of the ubiquitin ATG, and the ubiquitin polypeptide coding region is 228 bp plus 6 bp of a BamHI restriction site (SEQ ID NO. 96). This plasmid is designated pUCUbi7.

A nucleotide fragment coding for the lytic peptide corresponding to the amino acid sequence SEQ ID NO. 98) is generated as described in Example 2. The resulting Ubi7 ubiquitin-lytic peptide fusion gene construct corresponds to SEQ ID NO. 95. Unlike previous cloning attempts using the CaMV35S promoter as described in the Background section, the sequence does not reveal any point mutations in the lytic peptide sub-clones. The plasmid was stable in the *E. coli* host and did not inhibit its growth.

Figure 2:
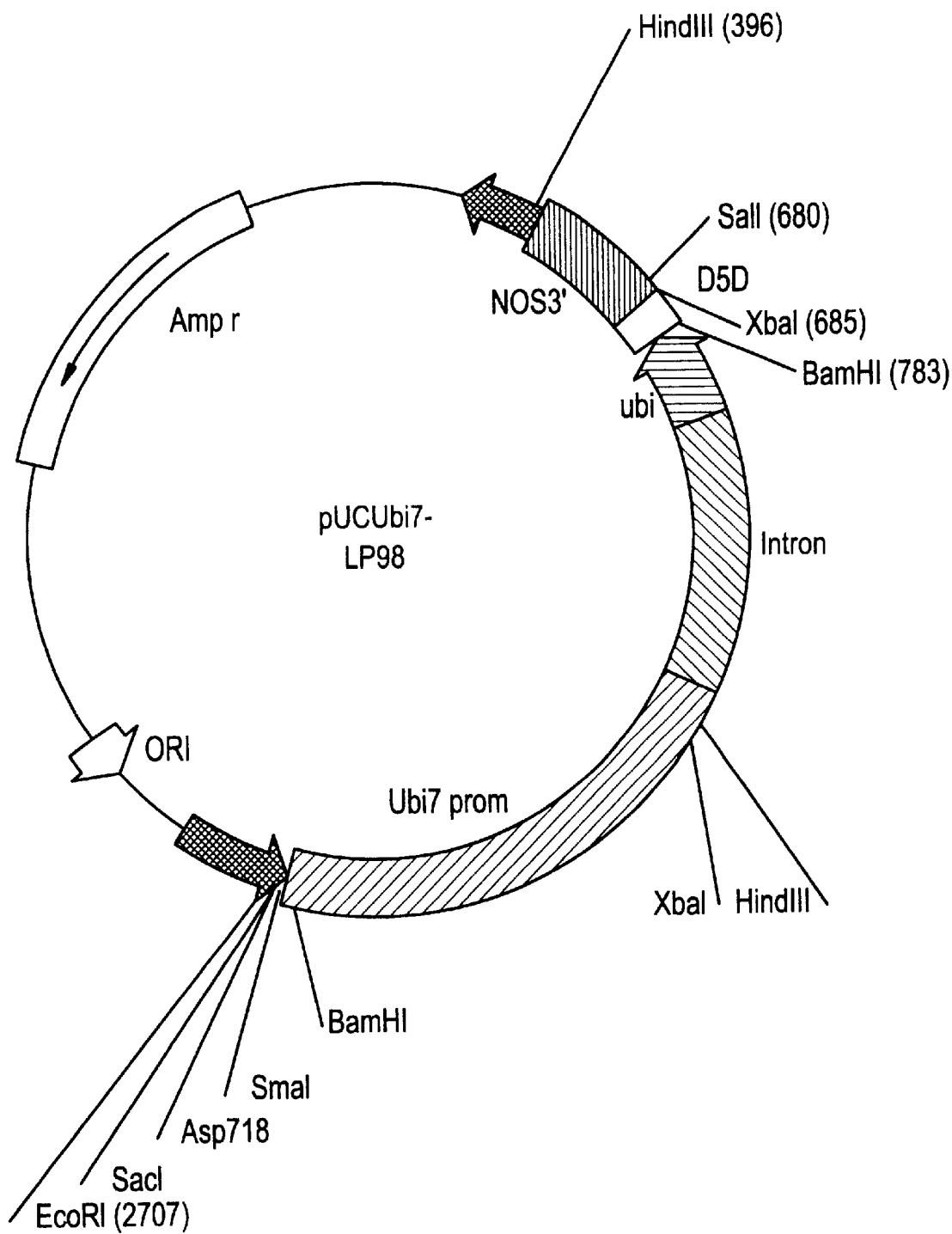
FIG. 2 is a map of a recombinant nucleic acid expression vector pUCUbi7-LP98 containing a 1220 bp polyubiquitin promoter region and 568 bp intron linked to a 228 bp coding region for a ubiquitin polypeptide with a six bp BamHI site at the 3' end (SEQ ID NO. 96) that is fused at its 3' end to a gene coding for a lytic peptide (D5D*, SEQ ID NO. 98). The Ubi7 ubiquitin-lytic peptide nucleotide sequence corresponds to SEQ ID NO. 95. A nopaline synthase polyadenylation signal is located at the 3' end of the lytic peptide gene.

The resulting pUC19 recombinant plasmid is shown in the plasmid map in FIG. 2. The sequence for the PCR insert containing the polyubiquitin promoter, intron, and the ubiquitin coding region corresponds to SEQ ID NO. 96 in Table 3 below. The sequence for the chimeric Ubi7 ubiquitin-lytic peptide fusion gene construct corresponds to SEQ ID NO. 95 in Table 3 below. This plasmid is designated as pUCUbi7-LP98.

The entire Ubi7 ubiquitin-lytic peptide fusion gene construct, including the polyadenylation site, is isolated from pUC19 as an Asp718/partial HindIII restriction fragment (the intron has an internal HindIII site) and sub-cloned into the pCGN1547 Agrobacterium vector for use in plant transformation. This plasmid is designated pCGNUbi7-LP98.

TABLE 3

NUCLEOTIDE SEQUENCE OF POTATO POLYUBIQUITIN PROMOTER
REGION (UB17) AND UBIQUITIN CODING REGION INSERT, AND
UBIQUITINLYTIC PEPTIDE FUSION GENE CONSTRUCT

```
SEQ ID NO. 95
TTTATCAATC AGATTTGAAC ATATAAATAA ATATAAATTG TCTCAATAAT          50

TCTACATTAA ACTAATATTT GAAATCTCAA TTTTATGATT TTTTAAATTC         100

ACTTTATATC CAAGACAATT TNCANCTTCA AAAAGTTTTA TTAAANATTT         150

ACATTAGTTT TGTTGATGAG GATGACAAGA TNTTGGTCAT CAATTCACTA         200

TACCCAAATT GAATAGTAAG CAACTTCAAT GTTTTTCATA ATGATAATGC         250

CAGACACAAN NNAAACCCAT TTATTATTCA CATTGATTGA GTTTTATATG         300

CAATATAGTA ATAATAATAA TATTTCTTAT AAAGCAAGAG GTCAATTTTT         350

TTTTAATTAT ACCACGTCAC TAAATTATAT TTGATAATGT AAAACAATTC         400

AAATTTTACT TAAATATCAT GAAATAAACT ATTTTTATAA CCAAATTACT         450

AAATTTTTCC AATAAAAAAA AGTCATTAAG AAGACATAAA ATAAATTTGA         500

GGTAAANGAG TGAAGTCGAC TGACTTTTTT TTTTTTTATC ATAAGAAAAT         550

AAATTATTAA CTTTAACCTA ATAAAACACT AATATAATTT CATGGAATCT         600

AATACTTACC TCTTAGAAAT AAGAAAAAGT GTTTCTAATA GACCCTCAAT         650

TTACATTAAA TATTTTCAAT CAAATTTAAA TAACAAATAT CAATATGAGG         700

TCAATAACAA TATCAAAATA ATATGAAAAA AGAGCAATAC ATAATATAAG         750

GGACGATTTA AGTGCGATTA TCAAGGTAGT ATTATATCCT AATTTGCTAA         800

TATTTGNGCT CTTATATTTA AGGTCATGTT CATGATAAAC TTGAAATGCG         850

CTATATTAGA GCATATATTA AAATAAAAAA ATACCTAAAA TAAAATTAAG         900

TTATTTTTAG TATATATTTT TTTACATGAC CTACATTTTT CTGGGTTTTT         950

CTAAAGGAGC GTGTAAGTGT CGACCTCATT CTCCTAATTT TCCCCACCAC        1000

ATAAAAATTA AAAAGGAAAG GTAGCTTTTG CGTGTTGTTT TGGTACACTA        1050

CACCTCATTA TTACACGTGT CCTCATATAA TTGGTTAACC CTATGAGGCG        1100

GTTTCGTCTA GAGTCGGCCA TGCCATCTAT AAAATGAAGC TTTCTGCACC        1150

TCATTTTTTT CATCTTCTAT CTGATTTCTA TTATAATTTC TCTCAATTGC        1200

CTTCAAATTT CTCTTTAAGG TTAGAATCTT CTCTATTTTT                   1240

GGTTTTTGTA TGTTTAGATT CTCGAATTAG CTAATCAGGC GCTGTTATAG        1290

CCCTTCCTTT TGAGTCTCTC CTCGGTTGTC TTGATGGAAA AGGCCTAACA        1340

TTTGAGTTTT TTTACGTCTG GTTTGATGGA AAAGGCCTAC AATTGGCCGT        1390

TTTCCCCGTT CGTTTTGATG AAAAAGCCCC TAGTTTGAGA TTTTTTTTCT        1440

GTCGTTCGTT CTAAAGGTTT AAAATTAGAG TTTTTACATT TGTTTGATGA        1490

AAAAGGCCTT AAATTTGAGT TTTTCCGGTT GATTTGATGA AAAAGCCCTA        1540

GAATTTGTGT TTTTCCGTCG GTTTGATTCT GAAGGCCTAA AATTTGAGTT        1590

TCTCCGGCTG TTTTGATGAA AAAGCCCTAA ATTTGAGTTT CTCCGGCTGT        1640

TTTGATGAAA AGCCCTAAA TTTGAAGTTT TTTCCCCGTG TTTTAGATTG        1690

TTTAGGTTTT AATTCTCGAA TCAGCTAATC AGGGAGTGTG AAAGCCCTAA        1740

ATTGAAGTTT TTTTCGTTGT TCTGATTGTT GTTTTTATGA ATTTGCAG         1788

ATG CAG ATC TTT GTG AAA ACT CTC ACC GGA AAG ACT ATC ACC       1830
```

TABLE 3-continued

NUCLEOTIDE SEQUENCE OF POTATO POLYUBIQUITIN PROMOTER REGION (UB17) AND UBIQUITIN CODING REGION INSERT, AND UBIQUITINLYTIC PEPTIDE FUSION GENE CONSTRUCT

```
CTA GAG GTG GAA AGT TCT GAT ACA ATC GAC AAC GTT AAG GCT      1872

AAG ATC CAG GAT AAG GAA GGA ATT CCC CCG GAT CAG CAA AGG      1914

CTT ATC TTC GCC GGA AAG CAG TTG GAG GAC GGA CGT ACT CTA      1956

GCT GAT TAC AAC ATC CAG AAG GAG TCT ACC CTC CAT TTG GTG      1998

CTC CGT CTA CGT GGA GGT GGA TCC GCT GTT AAA AGA GTG GGT      2040

CGT AGG TTG AAA AAG TTG GAC CGT AAG ATT GAT AGG TTA GGA      2082

GTT GAT TTT TGATCTAGAG TCGACCGATC CCCCGAATTT CCCCGA          2127
```

SEQ ID NO. 101
```
Met Gln Ile Phe Val Lys Thr Leu Thr Gly Lys Thr Ile Thr
 1               5                  10
Leu Glu Val Glu Ser Ser Asp Thr Ile Asp Asn Val Lys Ala
15                  20                  25
Lys Ile Glu Asp Lys Glu Gly Ile Pro Pro Asp Gln Gln Arg
        30                  35                  40
Leu Ile Phe Ala Gly Lys Gln Leu Glu Asp Gly Arg Thr Leu
            45                  50                  55
Ala Asp Tyr Asn Ile Gln Lys Glu Ser Thr Leu His Leu Val
                60                  65                  70
Leu Arg Leu Arg Gly Gly Gly Ser Ala Val Lys Arg Val Gly
                    75                  80
Arg Arg Leu Lys Lys Leu Asp Arg Lys Ile Asp Arg Leu Gly
85                  90                  95
Val Asp Phe
    100
```

SEQ ID NO. 96
```
TTTATCAATC AGATTTGAAC ATATAAATAA ATATAAATTG TCTCAATAAT        50

TCTACATTAA ACTAATATTT GAAATCTCAA TTTTATGATT TTTTAAATTC       100

ACTTTATATC CAAGACAATT TNCANCTTCA AAAAGTTTTA TTAAANATTT       150

ACATTAGTTT TGTTGATGAG GATGACAAGA TNTTGGTCAT CAATTACATA       200

TACCCAAATT GAATAGTAAG CAACTTCAAT GTTTTTCATA ATGATAATGA       250

CAGACACAAN NNAAACCCAT TTATTATTCA CATTGATTGA GTTTTATATG       300

CAATATAGTA ATAATAATAA TATTTCTTAT AAAGCAAGAG GTCAATTTTT       350

TTTTAATTAT ACCACGTCAC TAAATTATAT TTGATAATGT AAAACAATTC       400

AAATTTTACT TAAATATCAT GAAATAAACT ATTTTTATAA CCAAATTACT       450

AAATTTTTCC AATAAAAAAA AGTCATTAAG AAGACATAAA ATAAATTTGA       500

GGTAAANGAG TGAAGTCGAC TGACTTTTTT TTTTTTTATC ATAAGAAAAT       550

AAATTATTAA CTTTAACCTA ATAAAACACT AATATAATTT CATGGAATCT       600

AATACTTACC TCTTAGAAAT AAGAAAAAGT GTTTCTAATA GACCCTCAAT       650

TTACATTAAA TATTTTCAAT CAAATTTAAA TAACAAATAT CAATATGAGG       700

TCAATAACAA TATCAAAATA ATATGAAAAA AGAGCAATAC ATAATATAAG       750

GGACGATTTA AGTGCGATTA TCAAGGTAGT ATTATATCCT AATTTGCTAA       800

TATTTGNGCT CTTATATTTA AGGTCATGTT CATGATAAAC TTGAAATGCG       850

CTATATTAGA GCATATATTA AAATAAAAAA ATACCTAAAA TAAAATTAAG       900
```

TABLE 3-continued

NUCLEOTIDE SEQUENCE OF POTATO POLYUBIQUITIN PROMOTER
REGION (UB17) AND UBIQUITIN CODING REGION INSERT, AND
UBIQUITINLYTIC PEPTIDE FUSION GENE CONSTRUCT

```
TTATTTTTAG TATATATTTT TTTACATGAC CTACATTTTT CTGGGTTTTT    950

CTAAAGGAGC GTGTAAGTGT CGACCTCATT CTCCTAATTT TCCCCACCAC   1000

ATAAAAATTA AAAAGGAAAG GTAGCTTTTG CGTGTTGTTT TGGTACACTA   1050

CACCTCATTA TTACACGTGT CCTCATATAA TTGGTTAACC CTATGAGGCG   1100

GTTTCGTCTA GAGTCGGCCA TGCCATCTAT AAAATGAAGC TTTCTGCACC   1150

TCATTTTTTT CATCTTCTAT CTGATTTCTA TTATAATTTC TCTCAATTGC   1200

CTTCAAATTT CTCTTTAAGG TTAGAATCTT CTCTATTTTT             1240

GGTTTTTGTA TGTTTAGATT CTCGAATTAG CTAATCAGGC GCTGTTATAG   1290

CCCTTCCTTT TGAGTCTCTC CTCGGTTGTC TTGATGGAAA AGGCCTAACA   1340

TTTGAGTTTT TTTACGTCTG GTTTGATGGA AAAGGCCTAC AATTGGCCGT   1390

TTTCCCCGTT CGTTTTGATG AAAAAGCCCC TAGTTTGAGA TTTTTTTTCT   1440

GTCGTTCGTT CTAAAGGTTT AAAATTAGAG TTTTTACATT TGTTTGATGA   1490

AAAAGGCCTT AAATTTGAGT TTTTCCGGTT GATTTGATGA AAAAGCCCTA   1540

GAATTTGTGT TTTTCCGTCG GTTTGATTCT GAAGGCCTAA AATTTGAGTT   1590

TCTCCGGCTG TTTTGATGAA AAAGCCCTAA ATTTGAGTTT CTCCGGCTGT   1640

TTTGATGAAA AAGCCCTAAA TTTGAAGTTT TTTCCCCGTG TTTTAGATTG   1690

TTTAGGTTTT AATTCTCGAA TCAGCTAATC AGGGAGTGTG AAAGCCCTAA   1740

ATTGAAGTTT TTTTCGTTGT TCTGATTGTT GTTTTTATGA ATTTGCAG    1788

ATG CAG ATC TTT GTG AAA ACT CTC ACC GGA AAG ACT ATC ACC  1830

CTA GAG GTG GAA AGT TCT GAT ACA ATC GAC AAC GTT AAG GCT  1872

AAG ATC CAG GAT AAG GAA GGA ATT CCC CCG GAT CAG CAA AGG  1914

CTT ATC TTC GCC GGA AAG CAG TTG GAG GAC GGA CGT ACT CTA  1956

GCT GAT TAC AAC ATC CAG AAG GAG TCT ACC CTC CAT TTG GTG  1998

CTC CGT CTA CGT GGA GGT GGA TCC                          2022

SEQ ID NO. 102
Met Gln Ile Phe Val Lys Thr Leu Thr Gly Lys Thr Ile Thr
 1               5                  10

Leu Glu Val Glu Ser Ser Asp Thr Ile Asp Asn Val Lys Ala
15              20                  25

Lys Ile Glu Asp Lys Glu Gly Ile Pro Pro Asp Gln Gln Arg
    30              35                  40

Leu Ile Phe Ala Gly Lys Gln Leu Glu Asp Gly Arg Thr Leu
        45              50                  55

Ala Asp Tyr Asn Ile Gln Lys Glu Ser Thr Leu His Leu Val
            60                  65                  70

Leu Arg Leu Arg Gly Gly Ser
                75
```

EXAMPLE 4
Construction of Ubiquitin-Lytic Peptide Fusion Gene Plasmid Vectors pUc19 and pCGN1547 plasmid vectors containing a potato (*Solanum tuberosum*) Ubi3 promoter, a region coding for a ubiquitin polypeptide, and a gene coding for a lytic peptide are constructed according to Example 2. Each plasmid respectively contains one lytic peptide nucleotide sequence coding for an amino acid sequence corresponding to SEQ ID NO. 1, 7, 15, 21, 30, 39, 43, 52, 83, 86, 88, 90, and 91. The resultant pUC19 Ubi3 ubiquitin-lytic peptide recombinant plasmids are designated as follows: pUCUbi3-

LP1, pUCUbi3-LP7, pUCUbi3-LP15, pUCUbi3-LP21, pUCUbi3-LP30, pUCUbi3-LP39, pUCUbi3-LP43, pUCUbi3-LP52, pUCUbi3-LP83, pUCUbi3-LP86, pUCUbi3-LP88, pUCUbi3-LP90, and pUCUbi3-LP91. The resultant pCGN1547 Ubi3 ubiquitin-lytic peptide recombinant plasmids are designated as follows: pCGNUbi3-LP1, pCGNUbi3-LP7, pCGNUbi3-LP15, pCGNUbi3-LP21, pCGNUbi3-LP30, pCGNUbi3-LP39, pCGNUbi3-LP43, pCGNUbi3-LP52, pCGNUbi3-LP83, pCGNUbi3-LP86, pCGNUbi3-LP88, pCGNUbi3-LP90, and pCGNUbi3-LP91.

pUC19 and pCGN1547 plasmid vectors containing a potato (*Solanum tuberosum*) Ubi7 promoter and intron, a region coding for a ubiquitin polypeptide, and a gene coding for a lytic peptide are constructed according to Example 3. Each plasmid respectively contains one lytic peptide nucleotide sequence coding for an amino acid sequence corresponding to SEQ ID NO. 1, 7, 15, 21, 30, 39, 43, 52, 83, 86, 88, 90, and 91. The resultant pUC19 Ubi7 ubiquitin-lytic peptide recombinant plasmids are designated as follows: pUCUbi7-LP1, pUCUbi7-LP7, pUCUbi7-LP15, pUCUbi7-LP21, pUCUbi7-LP30, pUCUbi7-LP39, pUCUbi7-LP43, pUCUbi7-LP52, pUCUbi7-LP83, pUCUbi7-LP86, pUCUbi7-LP88, pUCUbi7-LP90, and pUCUbi7-LP91. The resultant pCGN1547 Ubi7 ubiquitin-lytic peptide recombinant plasmids are designated as follows: pCGNUbi7-LP1, pCGNUbi7-LP7, pCGNUbi7-LP15, pCGNUbi7-LP21, pCGNUbi7-LP30, pcGNUbi7-LP29, pCGNUbi7-LP43, pCGNUbi7-LP52, pCGNUbi7-LP83, pCGNUbi7-LF86, pCGNUbi7-LP88, pCGNUbi7-LP90, and pCGNUbi7-LP91.

EXAMPLE 5
Construction of GUS-Ubiquitin Fusion Gene Recombinant DNA Molecules and Ubiquitin Promoter-GUS Recombinant DNA Molecules Two chimeric genes containing a β-glucuronidase (GUS) reporter gene and the Ubi3 promoter were constructed in pCGN1547 plasmid vectors according to Garbarino, J., and Belknap, W., Plant Molecular Biology 24: 119 (1994), hereby incorporated by reference in its entirety. The first vector contains the 920 bp Ubi3 promoter ligated to the GUS gene, and expresses the GUS protein. This plasmid is designated pCGNUbi3-GUS. The second vector contains the 920 bp Ubi3 promoter and 228 bp ubiquitin coding region ligated in frame to the GUS gene. This plasmid expresses a ubiquitin-GUS fusion polypeptide. This plasmid is designated pCGNUbi3-GUSf.

Two chimeric genes containing a β-glucuronidase (GUS) reporter gene and the Ubi7 promoter minus the intron region were constructed in pCGN1547 plasmid vectors using PCR, as described in Example 3 and in Garbarino, J., and Belknap, W., Plant Molecular Biology 24: 119 (1994). The first vector contains a 1156 bp Ubi7 promoter region insert, including she 5' untranslated region of ubiquitin, ligated to the GUS gene. This plasmid does not contain the Ubi7 intron and expresses the GUS protein. This plasmid is designated pCGNUbi7-GUS. The second vector contains the 1156 Ubi7 ubiquitin promoter from pCGNUbi7-GUS and the 228 bp ubiquitin coding region fused in frame to the GUS reporter gene. This plasmid expresses a ubiquitin-GUS fusion polypeptide and is designated pCGNUbi7-GUSf.

EXAMPLE 6
Plant Transformation and GUS Gene Expression

The chimeric plasmids pCGNUbi3-GUS, pCGNUbi3-GUSf, pCGNUbi7-GUS, and pCGNUbi7-GUSf from Example 5 are introduced into the potato (*Solanum tuberosum*) using Agrobacterium mediated transformation according to Garbarino, J., and Belknap, W. Plant Molecular Biology 24:119 (1994). The strain of *Agrobacterium tumefaciens* used for transformation (PC2760, see An, G., et al., EMBO J. 4: 277 (1985)) harbors the disarmed Ti plasmid pAL4404 (see Hoekema, A., et al., Nature 303: 179 (1983). Plant transformation is carried out as previously described in Synder, G. W., et al., Plant Cell Rep 12:324 (1993), except that1 mg/l silver thiosulfate is added to the stage II transformation medium (see Chang, H. H., et al., Bot Bull Acad Sci 32: 63 (1991).

Expression of the ubiquitin-GUS fusion polypeptide and mRNA products and the GUS protein alone is examined by northern and western analysis, as described in Garbarino J., and Belknap, W., Plant Molecular Biology 24: 119 (1994). GUS protein expression is examined in the transgenic plants using western analysis. Although there is a wide range of activity among individual clones, the ubiquitin-GUS fusion polypeptide containing plants generally give 5–10 fold higher expression than the plants containing GUS protein alone. This higher level of protein expression corresponds to similarly elevated mRNA transcription levels for the ubiquitin-GUS fusion constructs, as shown by northern analysis (described in Garbarino et al., Plant Molecular Biology 24: 119 (1994)). Western analysis also shows that the ubiquitin-GUS fusion polypeptide was appropriately processed by endogenous ubiquitin hydrolases to produce free GUS protein.

GUS protein activity is measured as described by Jefferson, R. A., et al., EMBO J. 6: 3901 (1987). Table 4 below shows a comparison of the GUS activities in plants transformed with pCGNUbi3-GUS (ubi−) and plants transformed with pCGNUbi3-GUSf (ubi+). The activity is measured in nmoles methyl umbelliferon (MU) per mnute per milligram or protein. Methyl umbelliferon is the fluorescent product of the GUS enzymatic reaction.

TABLE 4

COMPARISON OF GUS PROTEIN ACTIVITY IN PLANTS TRANSFORMED WITH THE UBI3 PROMOTER WITH (+UBI) AND WITHOUT (−UBI) UBIQUITIN POLYPEPTIDE FUSION

| | GUS Activity (nmoles MU/min/mg protein) | | | | |
|---|---|---|---|---|---|
| Construct | Leaf Meristem | 2nd Leaf | 5th Leaf | Senescent Leaf | Tuber |
| 3.2 − ubi | 6.31 ± 0.74 | 2.51 ± 0.52 | 1.79 ± 0.22 | 5.42 ± 1.24 | 3.26 ± 0.27 |
| 8.1 − ubi | 25.8 ± 2.08 | 9.98 ± 2.10 | 6.34 ± 1.00 | 19.20 ± 6.11 | 14.2 ± 1.6 |
| 3.5 + ubi | 94.8 ± 12.6 | 60.3 ± 25.1 | 32.7 ± 8.71 | 50.1 ± 11.6 | 37.6 ± 10.4 |
| 9.8 + ubi | 33.3 ± 0.5 | 18.9 ± 2.75 | 9.74 ± 0.99 | 22.7 ± 3.57 | 20.7 ± 3.45 |

EXAMPLE
Plant Transformation and Ubiquitin-Lytic Peptide Gene Expression

The chimeric plasmids pCGNUbi3-LP98 from Example 2 and pCGNUbi7-LP98 from Example 3 are introduced into the potato (*Solanum tuberosum*) using Agrobacterium mediated transformation according to Garbarino, J., and Belknap, W. Plant Molecular Biology 24:119 (1994). The strain of *Agrobacterium tumefacians* used for transformation (PC2760, see An, G., et al., EMBO J. 4: 277 (1985)) harbors the disarmed Ti plasmid pAL4404 (see Hoekema, A., et al., Nature 303: 179 (1983). Plant transformation is carried out as previously described in Synder, G. W., et al., Plant Cell Rep 12:324 (1993), except that 1 mg/l silver thiosulfate is added to the stage II transformation medium (see Chang, H. H., et al., Bot Bull Acad Sci 32: 63 (1991).

Expression of the ubiquitin-lytic peptide fusion polypeptide and mRNA products is examined by northern and western analysis, in Garbarino J., and Belknap, W., Plant Molecular Biology 24: 119 (1994). Northern analysis shows that ubiquitin-lytic peptide mRNA is transcribed from the gene construct in the transgenic plants. Western analysis shows that the ubiquitin-lytic peptide fusion polypeptide is appropriately processed by endogenous ubiquitin hydrolases to produce free lytic peptide.

EXAMPLE 8

Cloned Ubi3/Ubi7 Promoter Activity mRNA expression from the cloned Ubi3 promoter was examined before and after wounding to determine if the cloned Ubi3 promoter is wound inducible in transformed plants (see Garbarino, J. and Belknap, W., Plant Molecular Biology 24:119 (1994)). Northern analysis comparing endogenous Ubi3 mRNA expression levels to pCGNUbi3-GUS and pCGNUbi3-GUSf mRMA expression levels in transformed plants (see Example 5) shows that while the endogenous Ubi3 mRNA transcription increases upon wounding, transcription from the recombinant Ubi3 plasmids does not. Thus the recombinant Ubi3 promoter does not have the wound inducible characteristic of the endogenous Ubi3 promoter. This result suggests that the 920 bp of upstream sequence cloned n the Ubi3 genomic clone is not sufficient to obtain wound-dependent activation of the promoter. The promoter instead is constitutive, however, it still demonstrates developmental regulation, as shown in Table 4 above.

In contrast, the cloned Ubi7 promoter retains its wound-dependent induction. Northern analysis comparing the endogenous Ubi7 mRNA expression levels to the expression levels from pCGNUbi7-GUS and pCGNUbi7-GUSf in transformed plants (see Example 5) shows that both the endogenous and the cloned Ubi7 promoter have wound-dependent activation.

Deposit Information

E. coli cultures, each respectively transformed with pUCUbi7-LP98 (Local Accession No. PBT-0273), pUCUbi3-LP98 (Local Accession No. PBT-0276), pUCUbi7 (Local Accession No. PBT-0277), and pUCUbi3 (Local Accession No. PBT-0234) were deposited in the Agricultural Research Service Culture Collection (NRRL). The depository is located at located at 1815 North University Street, Peoria, Ill., 61604.

What is claimed is:

1. A promoter comprising the sequence of nucleotides 1–1,788 of SEQ ID NO. 96.

2. A promoter comprising the sequence of nucleotides 1–1220 of SEQ ID NO. 96.

* * * * *